(12) United States Patent
Libbus et al.

(10) Patent No.: US 8,768,462 B2
(45) Date of Patent: Jul. 1, 2014

(54) SYSTEM AND METHOD FOR FILTERING NEURAL STIMULATION

(75) Inventors: Imad Libbus, St. Paul, MN (US); Scot C. Boon, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/483,846

(22) Filed: May 30, 2012

(65) Prior Publication Data

US 2012/0239101 A1 Sep. 20, 2012

Related U.S. Application Data

(62) Division of application No. 10/982,001, filed on Nov. 4, 2004, now Pat. No. 8,200,331.

(51) Int. Cl.
*A61N 1/00* (2006.01)

(52) U.S. Cl.
USPC .................................. 607/9; 607/2

(58) Field of Classification Search
USPC ....................................... 607/2, 9
See application file for complete search history.

(56) References Cited

U.S. PATENT DOCUMENTS

| | | | |
|---|---|---|---|
| 4,161,945 A * | 7/1979 | Grossman ................. | 600/508 |
| 4,206,398 A | 6/1980 | Janning | |
| 4,243,045 A * | 1/1981 | Maas ....................... | 600/508 |
| 4,251,118 A | 2/1981 | Rothen et al. | |
| 4,257,098 A | 3/1981 | Lacy | |
| 4,436,093 A * | 3/1984 | Belt ......................... | 607/9 |
| 4,627,441 A * | 12/1986 | Martin ..................... | 600/509 |
| 4,646,258 A * | 2/1987 | Miodownik .............. | 708/819 |
| 4,646,754 A | 3/1987 | Seale | |
| 4,791,931 A | 12/1988 | Slate | |
| 4,876,737 A | 10/1989 | Woodworth et al. | |
| 5,046,101 A | 9/1991 | Lovejoy | |
| 5,111,815 A | 5/1992 | Mower | |
| 5,190,035 A | 3/1993 | Salo et al. | |
| 5,199,428 A | 4/1993 | Obel et al. | |
| 5,203,326 A | 4/1993 | Collins | |

(Continued)

FOREIGN PATENT DOCUMENTS

| | | | |
|---|---|---|---|
| EP | 0547734 A2 | 6/1993 | |
| EP | 0581262 A1 | 2/1994 | |

(Continued)

OTHER PUBLICATIONS

"U.S. Appl. No. 10/746,847, Examiner Interview Summary mailed Jun. 16, 2009", 9 pgs.

(Continued)

*Primary Examiner* — Niketa Patel
*Assistant Examiner* — William Levicky
(74) *Attorney, Agent, or Firm* — Schwegman Lundberg & Woessner, P.A.

(57) ABSTRACT

Various aspects of the present subject matter provide a filter module. In various embodiments, the filter module comprises an input, an output, a signal path from the input to the output, a filter and a switch. The filter has a transfer response to attenuate a frequency of a neural stimulation signal. The switch is adapted to place the filter in the signal path when the neural stimulation signal is applied and to remove the filter from the signal path when the neural stimulation signal is not applied. Other aspects are provided herein.

20 Claims, 17 Drawing Sheets

(56) References Cited

U.S. PATENT DOCUMENTS

| | | |
|---|---|---|
| 5,243,980 A | 9/1993 | Mehra |
| 5,318,592 A | 6/1994 | Schaldach |
| RE34,663 E | 7/1994 | Seale |
| 5,330,507 A | 7/1994 | Schwartz |
| 5,334,221 A | 8/1994 | Bardy |
| 5,356,425 A | 10/1994 | Bardy et al. |
| 5,411,531 A | 5/1995 | Hill et al. |
| 5,437,285 A | 8/1995 | Verrier et al. |
| 5,477,858 A | 12/1995 | Norris et al. |
| 5,507,784 A | 4/1996 | Hill et al. |
| 5,513,644 A | 5/1996 | McClure et al. |
| 5,522,854 A | 6/1996 | Ideker et al. |
| 5,578,061 A | 11/1996 | Stroetmann et al. |
| 5,658,318 A | 8/1997 | Stroetmann et al. |
| 5,662,689 A | 9/1997 | Elsberry et al. |
| 5,700,282 A | 12/1997 | Zabara |
| 5,792,187 A | 8/1998 | Adams |
| 5,796,703 A | 8/1998 | Schell et al. |
| 5,817,131 A | 10/1998 | Elsberry et al. |
| 5,875,158 A | 2/1999 | Schell |
| 5,913,876 A | 6/1999 | Taylor et al. |
| 5,916,239 A | 6/1999 | Geddes et al. |
| 6,006,122 A | 12/1999 | Smits |
| 6,006,134 A | 12/1999 | Hill et al. |
| 6,035,233 A | 3/2000 | Schroeppel et al. |
| 6,058,331 A | 5/2000 | King |
| 6,073,048 A | 6/2000 | Kieval et al. |
| 6,134,470 A | 10/2000 | Hartlaub |
| 6,141,590 A | 10/2000 | Renirie et al. |
| 6,161,042 A | 12/2000 | Hartley et al. |
| 6,169,918 B1 | 1/2001 | Haefner et al. |
| 6,181,966 B1 | 1/2001 | Nigam |
| 6,208,902 B1 | 3/2001 | Boveja |
| 6,240,314 B1 | 5/2001 | Plicchi et al. |
| 6,240,316 B1 | 5/2001 | Richmond et al. |
| 6,266,564 B1 | 7/2001 | Hill et al. |
| 6,272,377 B1 | 8/2001 | Sweeney et al. |
| 6,285,907 B1 | 9/2001 | Kramer et al. |
| 6,341,236 B1 | 1/2002 | Osorio et al. |
| 6,349,233 B1 | 2/2002 | Adams |
| 6,371,922 B1 | 4/2002 | Baumann et al. |
| 6,400,982 B2 | 6/2002 | Sweeney et al. |
| 6,421,557 B1 | 7/2002 | Meyer |
| 6,522,926 B1 | 2/2003 | Kieval et al. |
| 6,600,954 B2 | 7/2003 | Cohen et al. |
| 6,610,713 B2 | 8/2003 | Tracey |
| 6,622,041 B2 | 9/2003 | Terry, Jr. et al. |
| 6,668,191 B1 | 12/2003 | Boveja |
| 6,741,529 B1 | 5/2004 | Getreuer |
| RE38,654 E | 11/2004 | Hill et al. |
| RE38,705 E | 2/2005 | Hill et al. |
| 6,900,708 B2 | 5/2005 | White et al. |
| 6,928,320 B2 | 8/2005 | King |
| 6,928,326 B1 | 8/2005 | Levine |
| 6,934,583 B2 | 8/2005 | Weinberg et al. |
| 6,937,896 B1 | 8/2005 | Kroll |
| 7,031,474 B1 | 4/2006 | Yuen et al. |
| 7,123,961 B1 | 10/2006 | Kroll et al. |
| 7,460,906 B2 | 12/2008 | Libbus |
| 7,480,532 B2 | 1/2009 | Kieval et al. |
| 7,486,991 B2 | 2/2009 | Libbus et al. |
| 7,499,748 B2 | 3/2009 | Moffitt et al. |
| 7,548,780 B2 | 6/2009 | Libbus et al. |
| 7,551,958 B2 | 6/2009 | Libbus et al. |
| 7,555,341 B2 | 6/2009 | Moffitt et al. |
| 7,561,923 B2 | 7/2009 | Libbus et al. |
| 7,570,999 B2 | 8/2009 | Libbus et al. |
| 7,584,004 B2 | 9/2009 | Caparso et al. |
| 7,617,003 B2 | 11/2009 | Caparso et al. |
| 7,640,057 B2 | 12/2009 | Libbus et al. |
| 7,643,875 B2 | 1/2010 | Heil, Jr. et al. |
| 7,647,114 B2 | 1/2010 | Libbus |
| 7,657,312 B2 | 2/2010 | Pastore et al. |
| 7,706,884 B2 | 4/2010 | Libbus |
| 7,769,446 B2 | 8/2010 | Moffitt et al. |
| 7,869,881 B2 | 1/2011 | Libbus et al. |
| 7,881,782 B2 | 2/2011 | Libbus et al. |
| 8,200,331 B2 | 6/2012 | Libbus et al. |
| 2002/0010493 A1 | 1/2002 | Poezevara et al. |
| 2002/0026221 A1 | 2/2002 | Hill et al. |
| 2002/0026222 A1 | 2/2002 | Schauerte et al. |
| 2002/0058877 A1 | 5/2002 | Baumann et al. |
| 2002/0072776 A1 | 6/2002 | Osorio et al. |
| 2002/0077670 A1 | 6/2002 | Archer et al. |
| 2002/0165586 A1 | 11/2002 | Hill et al. |
| 2002/0188325 A1 | 12/2002 | Hill et al. |
| 2003/0045909 A1 | 3/2003 | Gross et al. |
| 2003/0060848 A1 | 3/2003 | Kieval et al. |
| 2003/0060858 A1 | 3/2003 | Kieval et al. |
| 2003/0065365 A1 | 4/2003 | Zhu et al. |
| 2003/0078623 A1 | 4/2003 | Weinberg et al. |
| 2003/0100924 A1 | 5/2003 | Foreman et al. |
| 2003/0149450 A1 | 8/2003 | Mayberg |
| 2003/0158584 A1 | 8/2003 | Cates et al. |
| 2003/0195578 A1 | 10/2003 | Perron et al. |
| 2003/0212440 A1 | 11/2003 | Boveja |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0015205 A1 | 1/2004 | Whitehurst et al. |
| 2004/0059383 A1 | 3/2004 | Puskas |
| 2004/0127947 A1 | 7/2004 | Kim et al. |
| 2004/0138721 A1 | 7/2004 | Osorio et al. |
| 2004/0172074 A1 | 9/2004 | Yoshihito |
| 2004/0193231 A1 | 9/2004 | David et al. |
| 2004/0199210 A1 | 10/2004 | Shelchuk |
| 2004/0215274 A1 | 10/2004 | Kerver et al. |
| 2004/0215289 A1 | 10/2004 | Fukui |
| 2005/0085864 A1 | 4/2005 | Schulman et al. |
| 2005/0096705 A1 | 5/2005 | Pastore et al. |
| 2005/0125044 A1 | 6/2005 | Tracey |
| 2005/0131467 A1 | 6/2005 | Boveja |
| 2005/0143779 A1 | 6/2005 | Libbus |
| 2005/0143785 A1 | 6/2005 | Libbus |
| 2005/0143787 A1 | 6/2005 | Boveja et al. |
| 2005/0149126 A1 | 7/2005 | Libbus |
| 2005/0149127 A1 | 7/2005 | Libbus |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149148 A1 | 7/2005 | King |
| 2005/0149155 A1 | 7/2005 | Scheiner et al. |
| 2005/0182288 A1 | 8/2005 | Zabara |
| 2005/0187584 A1 | 8/2005 | Denker et al. |
| 2005/0197675 A1* | 9/2005 | David et al. .................. 607/9 |
| 2005/0248418 A1 | 11/2005 | Govind et al. |
| 2005/0251216 A1 | 11/2005 | Hill et al. |
| 2006/0079945 A1 | 4/2006 | Libbus |
| 2006/0106429 A1 | 5/2006 | Libbus et al. |
| 2006/0116737 A1 | 6/2006 | Libbus |
| 2006/0206153 A1 | 9/2006 | Libbus et al. |
| 2006/0224188 A1 | 10/2006 | Libbus et al. |
| 2006/0241725 A1 | 10/2006 | Libbus |
| 2006/0271118 A1 | 11/2006 | Libbus et al. |
| 2006/0282131 A1 | 12/2006 | Caparso et al. |
| 2007/0142864 A1 | 6/2007 | Libbus et al. |
| 2007/0142871 A1 | 6/2007 | Libbus et al. |
| 2008/0021507 A1 | 1/2008 | Libbus et al. |
| 2008/0172104 A1 | 7/2008 | Kieval et al. |
| 2009/0177100 A1 | 7/2009 | Ternes |
| 2010/0010553 A1 | 1/2010 | Libbus et al. |

FOREIGN PATENT DOCUMENTS

| | | |
|---|---|---|
| EP | 1304135 A2 | 4/2003 |
| EP | 1421973 A2 | 5/2004 |
| EP | 1486232 A2 | 12/2004 |
| EP | 1541193 A1 | 6/2005 |
| WO | WO-9216257 A1 | 10/1992 |
| WO | WO-9965561 A1 | 12/1999 |

(56) References Cited

FOREIGN PATENT DOCUMENTS

| WO | WO-0234327 A2 | 5/2002 |
|---|---|---|
| WO | WO-02085448 A2 | 10/2002 |
| WO | WO-03011388 A2 | 2/2003 |
| WO | WO-03041559 A2 | 5/2003 |
| WO | WO-03076008 A1 | 9/2003 |
| WO | WO-2004084990 A1 | 10/2004 |
| WO | WO-2004084993 A1 | 10/2004 |
| WO | WO-2004110549 A2 | 12/2004 |
| WO | WO-2005053788 A1 | 6/2005 |
| WO | WO-2005063332 A1 | 7/2005 |
| WO | WO-2005113066 A1 | 12/2005 |
| WO | WO-2006031331 A1 | 3/2006 |
| WO | WO-2006098996 A1 | 9/2006 |
| WO | WO-2007078410 A1 | 7/2007 |

OTHER PUBLICATIONS

"U.S. Appl. No. 10/746,847, Final Office Action mailed Oct. 1, 2009", 10 pgs.
"U.S. Appl. No. 10/746,847, Non Final Office Action mailed Sep. 13, 2006", 14 pgs.
"U.S. Appl. No. 10/746,847, Non-Final Office Action mailed Mar. 2, 2007", 17 pgs.
"U.S. Appl. No. 10/746,847, Non-Final Office Action mailed Aug. 28, 2007", 18 pgs.
"U.S. Appl. No. 10/746,847, Preliminary Amendment filed Feb. 9, 2004", 5 pgs.
"U.S. Appl. No. 10/746,847, Response filed May 30, 2007 to Non Final Office Action mailed Mar. 2, 2007", 14 pgs.
"U.S. Appl. No. 10/746,847, Response filed Jul. 14, 2008 to Final Office Action mailed Feb. 25, 2008", 11 pgs.
"U.S. Appl. No. 10/746,847, Response filed Aug. 14, 2006 to Non Final Office Action mailed Jul. 14, 2006", 9 pgs.
"U.S. Appl. No. 10/746,847, Response filed Nov. 28, 2007 to Non Final Office Action mailed Aug. 28, 2007", 13 pgs.
"U.S. Appl. No. 10/746,847, Response filed Dec. 13, 2006 to Non Final Office Action mailed Sep. 13, 2006", 13 pgs.
"U.S. Appl. No. 10/746,847, Restriction Requirement mailed Jul. 14, 2006", 8 pgs.
"U.S. Appl. No. 10/746,847, Supplemental Amendment filed Jun. 22, 2009", 10 pgs.
"U.S. Appl. No. 10/746,847, Supplemental Preliminary Amendment filed Apr. 25, 2005", 8 pgs.
"U.S. Appl. No. 10/746,847, Supplemental Preliminary Amendment filed Sep. 23, 2004", 7 pgs.
"U.S. Appl. No. 10/982,001, Appeal Brief, mailed Nov. 13, 2009", 33 pgs.
"U.S. Appl. No. 10/982,001, Advisory Action mailed Jun. 9, 2010", 3 pgs.
"U.S. Appl. No. 10/982,001, Examiner Interview Summary filed Oct. 3, 2008", 2 pgs.
"U.S. Appl. No. 10/982,001, Examiner Interview Summary mailed Feb. 6, 2012", 3 pgs.
"U.S. Appl. No. 10/982,001, Examiner Interview Summary mailed Jun. 15, 2010", 3 pgs.
"U.S. Appl. No. 10/982,001, Examiner Interview Summary mailed Sep. 15, 2008", 4 pgs.
"U.S. Appl. No. 10/982,001, Final Office Action mailed Feb. 22, 2010", 10 pgs.
"U.S. Appl. No. 10/982,001, Final Office Action mailed Jun. 4, 2009", 15 pgs.
"U.S. Appl. No. 10/982,001, Non Final Office Action mailed Jun. 29, 2007", 7 pgs.
"U.S. Appl. No. 10/982,001, Non Final Office Action mailed Nov. 4, 2011", 11 pgs.
"U.S. Appl. No. 10/982,001, Non-Final Office Action mailed May 14, 2008", 8 pgs.
"U.S. Appl. No. 10/982,001, Non-Final Office Action mailed Dec. 29, 2008", 11 pgs.
"U.S. Appl. No. 10/982,001, Notice of Allowance mailed Feb. 14, 2012", 7 pgs.
"U.S. Appl. No. 10/982,001, Response filed Feb. 6, 2012 to Non Final Office Action mailed Nov. 4, 2011", 13 pgs.
"U.S. Appl. No. 10/982,001, Response filed Mar. 30, 2009 to Non Final Office Action mailed Dec. 29, 2008", 15 pgs.
"U.S. Appl. No. 10/982,001, Response filed Apr. 17, 2007 to Restriction Requirement mailed Apr. 4, 2007", 13 pgs.
"U.S. Appl. No. 10/982,001, Response filed May 24, 2010 to Final Office Action mailed Feb. 22, 2010", 9 pgs.
"U.S. Appl. No. 10/982,001, Response filed Jun. 17, 2010 to Advisory Action mailed Jun. 9, 2010", 8 pgs.
"U.S. Appl. No. 10/982,001, Response filed Aug. 14, 2008 to Non Final Office Action mailed May 14, 2008", 16 pgs.
"U.S. Appl. No. 10/982,001, Response filed Oct. 1, 2007 to Non Final Office Action mailed Jun. 29, 2007", 12 pgs.
"U.S. Appl. No. 10/982,001, Restriction Requirement mailed Apr. 4, 2007", 8 pgs.
"U.S. Appl. No. 11/000,249, Advisory Action mailed Jan. 26, 2011", 3 pgs.
"U.S. Appl. No. 11/000,249, Examiner Interview Summary mailed Aug. 27, 2010", 3 pgs.
"U.S. Appl. No. 11/000,249, Final Office Action mailed Jan. 14, 2010", 10 pgs.
"U.S. Appl. No. 11/000,249, Final Office Action mailed Oct. 13, 2010", 12 pgs.
"U.S. Appl. No. 11/000,249, Non Final Office Action mailed Apr. 13, 2011", 9 pgs.
"U.S. Appl. No. 11/000,249, Non-Final Office Action mailed Apr. 26, 2010", 7 pgs.
"U.S. Appl. No. 11/000,249, Non-Final Office Action mailed Jul. 15, 2009", 9 pgs.
"U.S. Appl. No. 11/000,249, Response filed Jan. 13, 2011 to Final Office Action mailed Oct. 13, 2010", 19 pgs.
"U.S. Appl. No. 11/000,249, Response filed Apr. 14, 2010 to Final Office Action mailed Jan. 14, 2010", 14 pgs.
"U.S. Appl. No. 11/000,249, Response filed Apr. 16, 2009 to Restriction Requirement mailed Mar. 30, 2009", 11 pgs.
"U.S. Appl. No. 11/000,249, Response filed Aug. 26, 2010 to Non Final Office Action mailed Apr. 26, 2010", 15 pgs.
"U.S. Appl. No. 11/000,249, Response filed Oct. 15, 2009 to Non Final Office Action mailed Jul. 15, 2009", 15 pgs.
"U.S. Appl. No. 11/000,249, Response filed Nov. 2, 2007 to Restriction Requirement mailed Oct. 2, 2007", 11 pgs.
"U.S. Appl. No. 11/000,249, Restriction Requirement mailed Mar. 30, 2009", 5 pgs.
"U.S. Appl. No. 11/000,249, Restriction Requirement mailed Oct. 2, 2007", 5 pgs.
"U.S. Appl. No. 11/077,970, Response filed Oct. 23, 2009 to Advisory Action mailed Oct. 6, 2009", 11 pgs.
"U.S. Appl. No. 11/312,178, Notice of Allowance mailed Apr. 3, 2009", 6 pgs.
"U.S. Appl. No. 11/621,194, Final Office Action mailed May 19, 2010", 8 pgs.
"U.S. Appl. No. 11/621,194, Non-Final Office Action mailed Oct. 1, 2009", 22 pgs.
"U.S. Appl. No. 11/621,194, Response filed Mar. 1, 2010 to Non Final Office Action mailed Oct. 1, 2009", 11 pgs.
"U.S. Appl. No. 11/621,194, Response filed Aug. 19, 2010 to Final Office Action mailed May 19, 2010", 8 pgs.
"U.S. Appl. No. 12/562,227, Examiner Interview Summary mailed Feb. 28, 2011", 3 pgs.
"U.S. Appl. No. 12/562,227, Final Office Action mailed Nov. 24, 2010", 12 pgs.
"U.S. Appl. No. 12/562,227, Non-Final Office Action mailed Jul. 13, 2010", 8 pgs.
"U.S. Appl. No. 12/562,227, Response filed Feb. 24, 2011 to Final Office Action mailed Nov. 24, 2010", 10 pgs.
"U.S. Appl. No. 12/562,227, Response filed Oct. 13, 2010 to Non Final Office Action mailed Jul. 13, 2010", 14 pgs.
"European Application Serial No. 05824915.2, Communication dated Sep. 10, 2007", 8 pgs.

(56) References Cited

OTHER PUBLICATIONS

"European Application Serial No. 05824915.2, Office Action mailed May 11, 2010", 6 pgs.

"European Application Serial No. 05824915.2, Response filed Mar. 20, 2008 to Communication dated Sep. 10, 2007", 22 pgs.

"European Application Serial No. 05824915.2, Response filed Nov. 5, 2010 to Office Action mailed May 11, 2010", 3 pgs.

"International Search Report and Written Opinion for Application No. PCT/US2005/039832, date mailed Mar. 14, 2006", 13 Pages.

"Japanese Application Serial No. 2007-540035, Office Action dated Jul. 19, 2011", (w/ English Translation), 4 pgs.

Bilgutay, A M, et al., "A new concept in the treatment of hypertension utilizing an implantable electronic device: "Baropacer"", Trans Am Soc Artif Intern Organs., 10, (1964), 387-395.

Bilgutay, A M, et al., "Vagal tuning for the control of supraventricular arrhythmias", Surgical Forum, 16, (1965), 151-3.

Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.

Courtice, G P, et al., "Effect of frequency and impulse pattern on the non-cholinergic cardiac response to vagal stimulation in the toad, Bufo marinus", Journal of the Autonomic Nervous System, 48(3), (Aug. 1994), 267-72.

Epstein, S. E., et al., "Treatment of angina pectoris by electrical stimulation of the carotid-sinus nerves", New England Journal of Medicine, 280(18), (May 1, 1969), 971-978.

Farrehi, C, "Stimulation of the carotid sinus nerve in treatment of angina pectoris", American Heart Journal, 80(6), (Dec. 1970), 759-65.

Feliciano, L, et al., "Vagal nerve stimulation releases vasoactive intestinal peptide which significantly increases coronary artery blood flow", Cardiovascular Research, 40(1), (Oct. 1998), 45-55.

Grassi, Guido, et al., "Baroreflex and non-baroreflex modulation of vagal cardiac control after myocardial infarction", Am J Cardiol., 84(5), (Sep. 1, 1999), 525-529.

Holder, L K, "Treatment of refractory partial seizures: preliminary results of a controlled study", Pacing & Clinical Electrophysiology, 15(10 Pt 2), (Oct. 1992), 1557-71.

Kendrick, J E, "A comparison of the cardiovascular responses to stimulation of the aortic and carotid sinus nerves of the dog", Proceedings of the Society for Experimental Biology & Medicine, 144(2), (Nov. 1973), 404-11.

Lacanette, Kerry, "A Basic Introduction to Filters—Active, Passive, and Switched-Capacitor", National Semiconductor Corporation, http://www.swarthmore.edu/NatSci/echeeve1/Ref/DataSheet/Inttofilters.pdf, (Apr. 1991), 1-22.

Libbus, I., "Integrated Lead for Applying Cardiac Resynchronization Therapy and Neural Stimulation Therapy", U.S. Appl. No. 11/077,970, filed Mar. 11, 2005, 67 pgs.

Libbus, I., et al., "Method and Apparatus for Synchronizing Neural Simulation to Cardiac Cycles", U.S. Appl. No. 11/099,141, filed Apr. 5, 2005, 36 pgs.

Libbus, Imad, "Automatic Neural Stimulation Modulation Based on Activity", U.S. Appl. No. 11/558,083, filed Nov. 9, 2006, 76 pgs.

Libbus, Imad, "Cardiac Rhythm Management Device With Neural Sensor", U.S. Appl. No. 10/992,320, filed Nov. 18, 2004, 65 pgs.

Libbus, Imad, "Neural Stimulation With Avoidance of Inappropriate Stimulation", U.S. Appl. No. 11/000,249, filed Nov. 30, 2004, 45 pgs.

Libbus, Imad, "Stimulator for Auricular Branch of Vagus Nerve", U.S. Appl. No. 11/005,703, filed Dec. 7, 2004, 35 pgs.

Libbus, Imad, "System to Provide Myocardial and Neural Stimulation", U.S. Appl. No. 11/087,935, filed Mar. 23, 2005, 52 pgs.

Neistadt, A, et al., "Effects of electrical stimulation of the carotid sinus nerve in reversal of experimentally induced hypertension", Surgery, 61(6), (Jun. 1967), 923-31.

Peters, T K, et al., "The principle of electrical carotid sinus nerve stimulation: a nerve pacemaker system for angina pectoris and hypertension therapy", Annals of Biomedical Engineering, 8(4-6), (1980), 445-458.

Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.

Ross, Jeffrey, et al., "Use of Extracellular Matrix and Electrical Therapy", U.S. Appl. No. 11/017,237, filed Dec. 20, 2004, 89 pgs.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

Sih, Harris J., "Implantable Medical Devices Comprising Isolated Extracellular Matrix", U.S. Appl. No. 11/017,432, filed Dec. 20, 2004, 87 pgs.

Vanoli, E., et al., "Vagal Stimulation and Prevention of Sudden Death in Conscious Dogs With a Healed Myocardial Infarction", Circulation Research, 68(5), (May 1991), 1471-1481.

Westlund, Randy, "Lead Electrode Incorporating Extracellular Matrix", U.S. Appl. No. 11/017,238, filed Dec. 20, 2004, 85 pgs.

\* cited by examiner

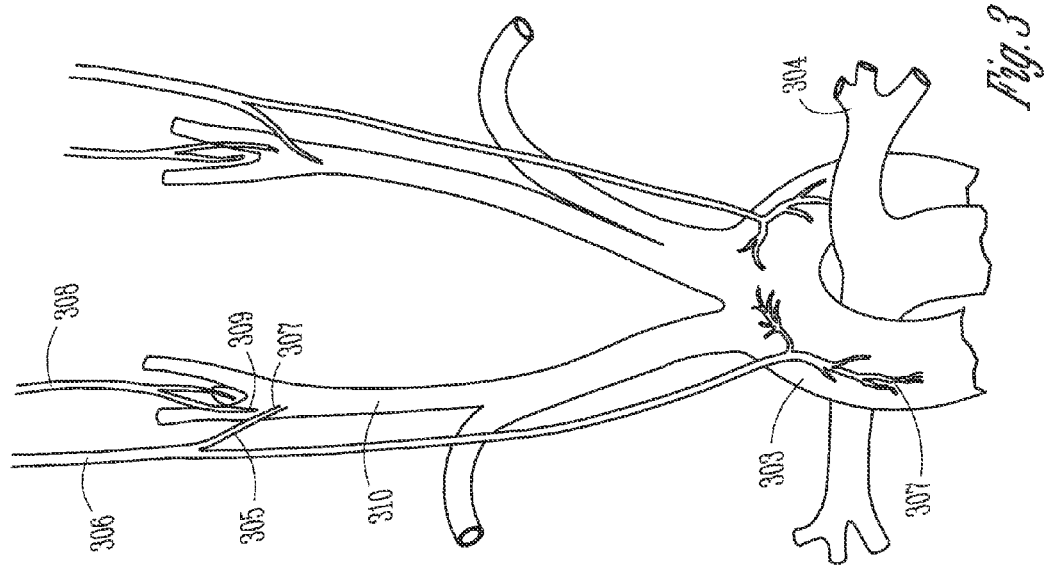
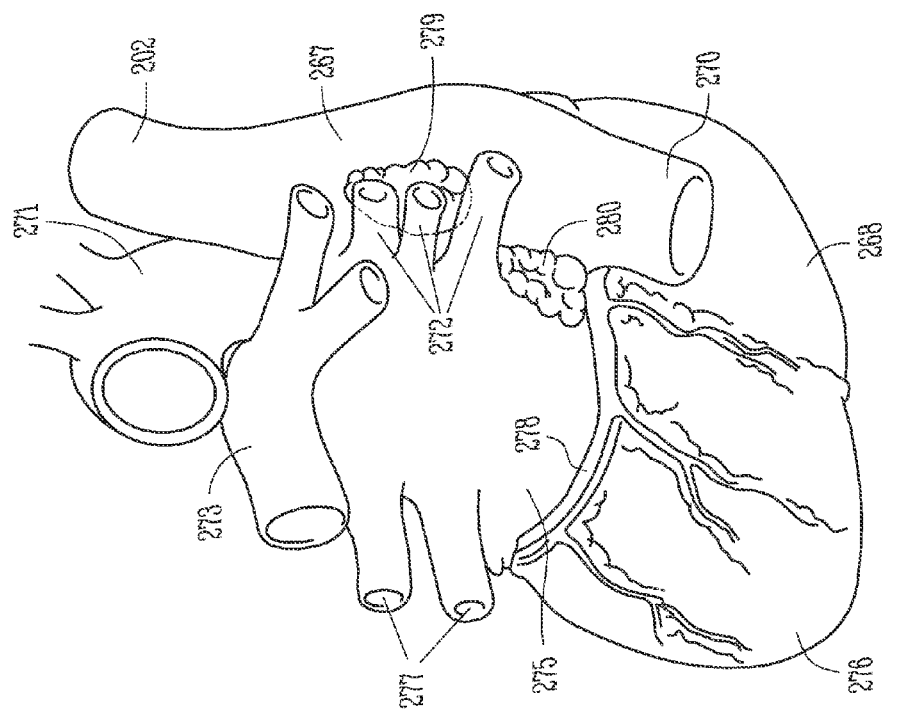

SYSTEM AND METHOD FOR FILTERING NEURAL STIMULATION

CLAIM OF PRIORITY

This application is a division of and claims the benefit of priority under 35 U.S.C. §120 to U.S. patent application Ser. No. 10/982,001, filed on Nov. 4, 2004, now issued as U.S. Pat. No. 8,200,331, which is hereby incorporated by reference herein in its entirety.

CROSS REFERENCE TO RELATED APPLICATIONS

The following commonly assigned U.S. patent application is related, and is incorporated by reference herein in its entirety: "Sensing With Compensation for Neural Stimulator," U.S. patent application Ser. No. 10/746,847, filed on Dec. 24, 2003, now abandoned.

TECHNICAL FIELD

This application relates generally to sensing electrical activity and, more particularly, to systems, devices and methods for filtering neural stimulation from sensed electrical signals.

BACKGROUND

Implanting a chronic electrical stimulator, such as a cardiac stimulator, to deliver medical therapy(ies) is known. Examples of cardiac stimulators include implantable cardiac rhythm management (CRM) devices such as pacemakers, implantable cardiac defibrillators (ICDs), and implantable devices capable of performing pacing and defibrillating functions.

Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

Heart failure refers to a clinical syndrome which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance.

Direct electrical stimulation has been applied to afferent nerve trunks, including the vagal nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension. Electrical systems have been proposed to treat hypertension in patients who do not otherwise respond to therapy involving lifestyle changes and hypertension drugs, and possibly to reduce drug dependency for other patients.

SUMMARY

When CRM and neural stimulation therapies are both provided, neural stimulation frequencies can fall in the passband of the CRM device' sense amplifier, thus resulting in improper sensing by the CRM device. The present subject matter provides, among other things, a CRM device capable of providing appropriate electrical sensing in the presence of neural stimulation artifacts.

Various aspects of the present subject matter provide a filter module. In various embodiments, the filter module comprises an input, an output, a signal path from the input to the output, a filter and a switch. The filter has a transfer response to attenuate a frequency of a neural stimulation signal. The switch is adapted to place the notch filter in the signal path when the neural stimulation signal is applied and to remove the notch filter from the signal path when the neural stimulation signal is not applied. In various embodiments, the filter includes a notch filter having a center frequency corresponding to a frequency of a neural stimulation signal. In various embodiments, multiple notch filters are used to filter harmonic of the neural stimulation signal. In various embodiments, a low pass filter is used.

Various aspects of the present subject matter provide a medical device. In various embodiments, the medical device comprises a filter module and a controller. The filter module is adapted to pass electrical signals indicative of a sensed electrical activity over a signal path. The filter module includes a filter selectively connected in the signal path. The filter has a transfer response to attenuate a frequency of a neural stimulation signal. The controller is adapted to receive a neural stimulation status signal, and to communicate with the sensing module to selectively route the signal path through the filter based on the status signal to filter the neural stimulation frequency from the electrical signals.

Various aspects of the present subject matter provide a system. In various embodiments, the system comprises means to sense cardiac activity as an electrical signal, means to receive an alert for neural stimulation, and filter means responsive to the alert to filter the neural stimulation from the electrical signal. In various embodiments, the system comprises a neural stimulation (NS) device and a cardiac rhythm management (CRM) device. The NS device includes a pulse generator, a controller and a communications interface. The controller is adapted to communicate with the pulse generator and implement a stimulation protocol to apply neural stimulation at a neural stimulation frequency. The communications interface is adapted to communicate with the controller and to send a neural stimulation status signal. The CRM device includes a controller, a port for connecting a lead with an electrode to sense cardiac activity, and a filter module. The filter module includes an input connected to the port, an output connected to the controller, and a signal path between the input and the output. The filter module further includes a filter having has a transfer response to attenuate a frequency of a neural stimulation signal. The controller of the CRM device is adapted to receive the neural stimulation status signal, and to selectively actuate the switch to connect the filter in the signal path when the status signal indicates that the neural stimulation device is applying neural stimulation and to remove the filter from the signal path when the status signal indicates that the neural stimulation device is not applying neural stimulation.

Various aspects of the present subject matter provide a method. In various embodiments of the method, an electrical signal indicative of sensed electrical activity is received and a neural stimulation alert regarding neural stimulation is received. In response to the neural stimulation alert, the electrical signal is filtered. A filter having a transfer response to attenuate a frequency of a neural stimulation signal is applied.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 2A-2C illustrate a heart.

FIG. 3 illustrates baroreceptors and afferent nerves in the area of the carotid sinuses and aortic arch.

DETAILED DESCRIPTION

Figure 1B:
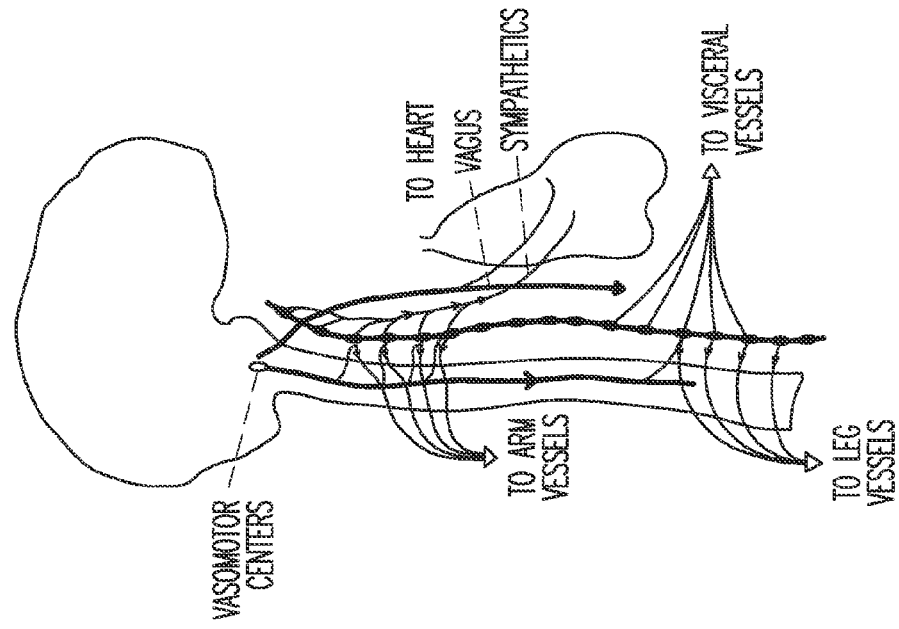
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the bill scope of legal equivalents to which such claims are entitled.

Potential neural stimulation sites such as the cardiac fat pads and great vessels, are in close proximity to CRM sensing leads. Extended periods of neural stimulation can occur at an amplitude and frequency capable of interfering with the electrical sensing for a CRM device. Electrical artifacts caused by neural stimulation may be misinterpreted by the CRM device, leading to the inappropriate delivery of therapy.

The present subject matter provides a CRM device capable of providing appropriate electrical sensing in the presence of neural stimulation artifacts. Whenever neural stimulation is applied, the CRM device is alerted to the presence of potentially disruptive electrical artifacts attributed to the neural stimulation, and switches to a notch filter mode to filter the neural stimulation from the electrogram. The CRM device uses the notch filter mode to provide appropriate sensing of the cardiac signal in the presence of electrical interference from the neural stimulator.

In addition to being alerted to the neural stimulation, various embodiments of the CRM device receive information regarding the frequency of neural stimulation. Some notch filter embodiments use a sampled data system, such as digital signal processing or switched-capacitor techniques, where a common clock source establishes both the neural stimulation frequency and the notch filter frequency. In these embodiments, the notch filter frequency tracks the neural stimulation frequency, such that the notch filter simultaneously provides a strong, narrow attenuation of the neural stimulation artifact and passes the cardiac signal with a large spectral energy. The CRM device remains in the notch filter mode during the period of neural stimulation, and returns to a default sensing mode after the neural stimulation.

The neural stimulation can be used to stimulate the baroreflex as part of a hypertension treatment. A brief description of hypertension and baroreflex is provided below, followed by various systems to provide neural stimulation and CRM therapies.

Hypertension and Baroreflex Physiology

A brief discussion of hypertension and the physiology related to baroreceptors is provided to assist the reader with understanding this disclosure. This brief discussion introduces hypertension, the autonomic nervous system, and baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
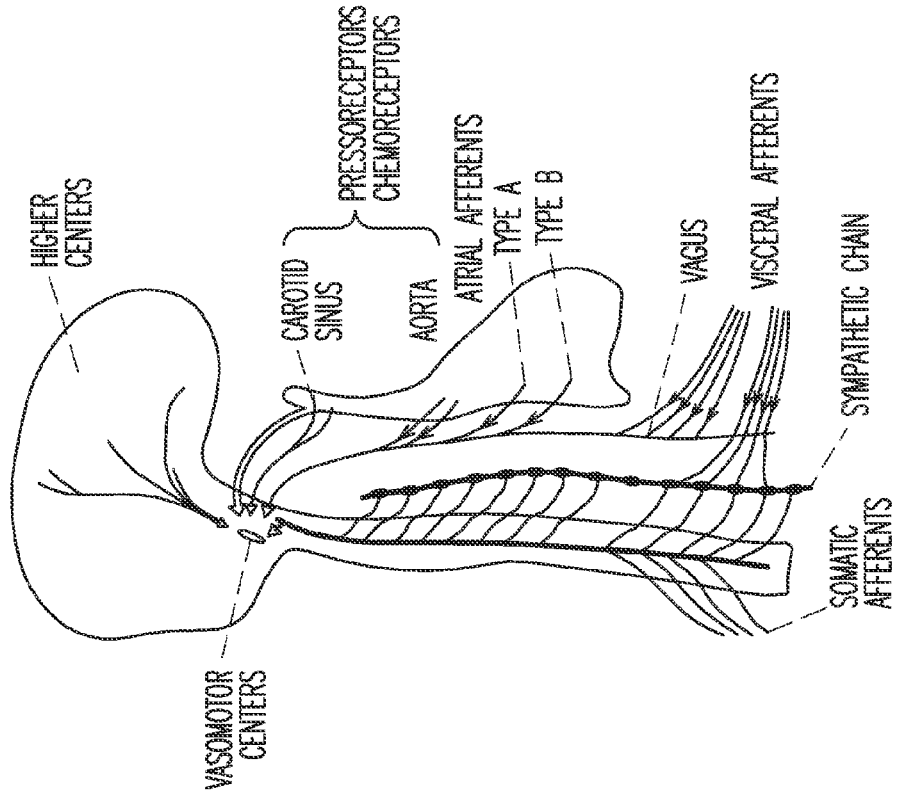

Various embodiments of the present subject matter provide neural stimulation to affect the heart rate, blood pressure, vasodilation and vasoconstriction. The heart rate and force is increased when the sympathetic nervous system is stimulated, and is decreased when the sympathetic nervous system is inhibited (the parasympathetic nervous system is stimulated). FIGS. 1A and 1B illustrate neural mechanisms for peripheral vascular control. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells, such as within a cardiac fat pad, can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figure 2B:
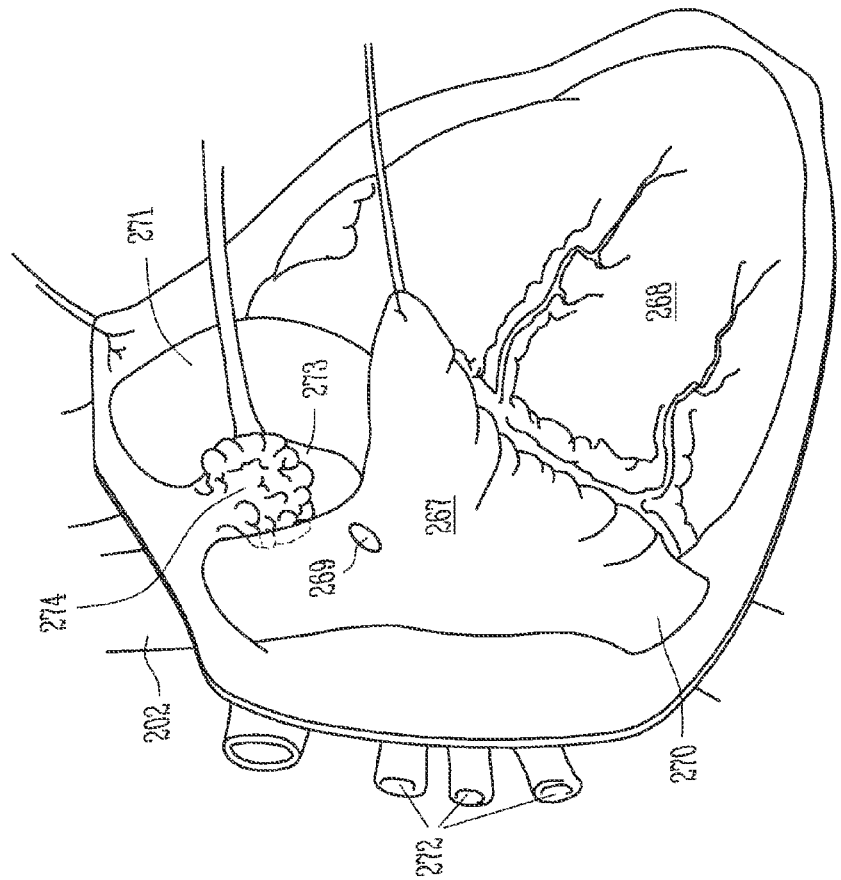
Figure 2A:
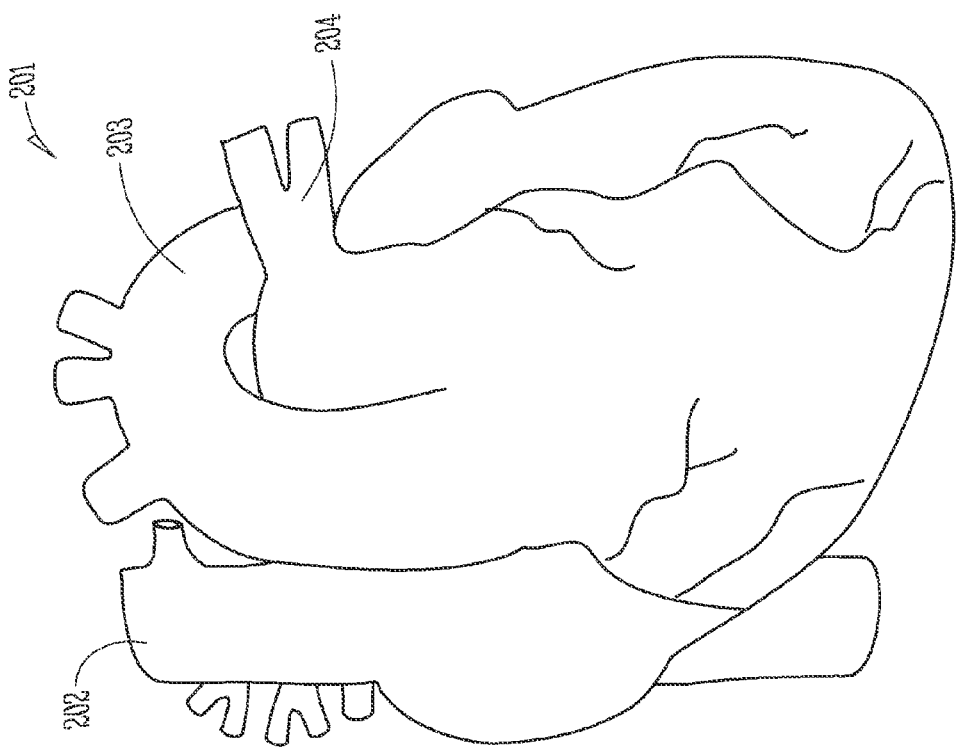

FIGS. 2A-2C illustrate a heart. As illustrated in FIG. 2A, the heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. In various embodiments, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreceptor stimulator intravascularly into the pulmonary artery.

FIGS. 2B-2C illustrate the right side and left side of the heart, respectively, and further illustrate cardiac fat pads which have ganglia or nerve endings that function baroreceptor sites. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Baroreceptor nerve endings in the cardiac fat pad 274 are stimulated in some embodiments using an electrode screwed or otherwise inserted into the fat pad, and are stimulated in some embodiments using an intravenously-fed lead proximately positioned to the fat pad in a vessel such as the right pulmonary artery or superior vena cava, for example. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins and a cardiac fat pad 280 located proximate to the inferior vena cava and left atrium. Baroreceptor nerve endings in the fat pad 279 are stimulated in some embodiments using an electrode screwed or otherwise inserted into the fat pad 279, and are stimulated in some embodiments using an intravenously-fed lead proximately positioned to the fat pad in a vessel such as the right pulmonary artery 273 or right pulmonary vein 272, for example. Baroreceptors in the cardiac fat pad 280 are stimulated in some embodiments using an electrode screwed or otherwise inserted into the fat pad, and are stimulated in some embodiments using an intravenously-fed lead proximately positioned to the fat pad in a vessel such as the inferior vena cava 270 or coronary sinus or a lead in the left atrium 275, for example.

FIG. 3 illustrates baroreceptors in the area of the carotid sinus 305, aortic arch 303 and pulmonary artery 304. The aortic arch 303 and pulmonary artery 304 were previously illustrated with respect to the heart in FIG. 2A. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

Figure 5:
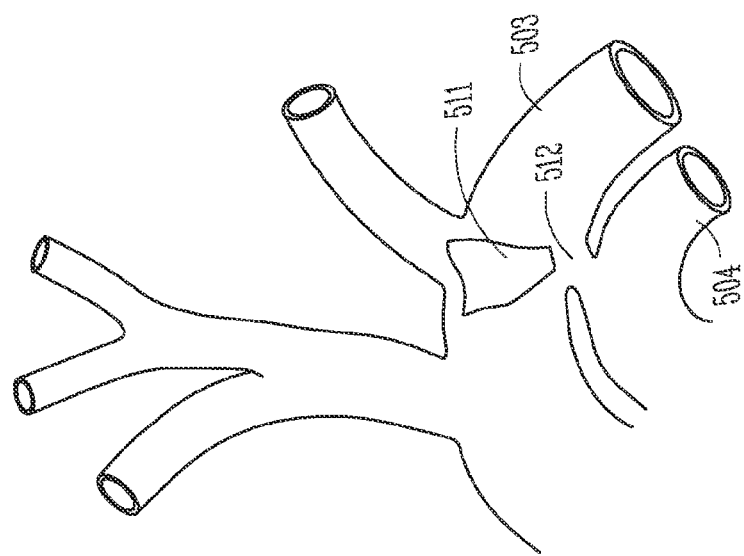
FIG. 5 illustrates baroreceptor fields in the aortic arch, the ligamentum arteriosum and the trunk of the pulmonary artery.
Figure 4:
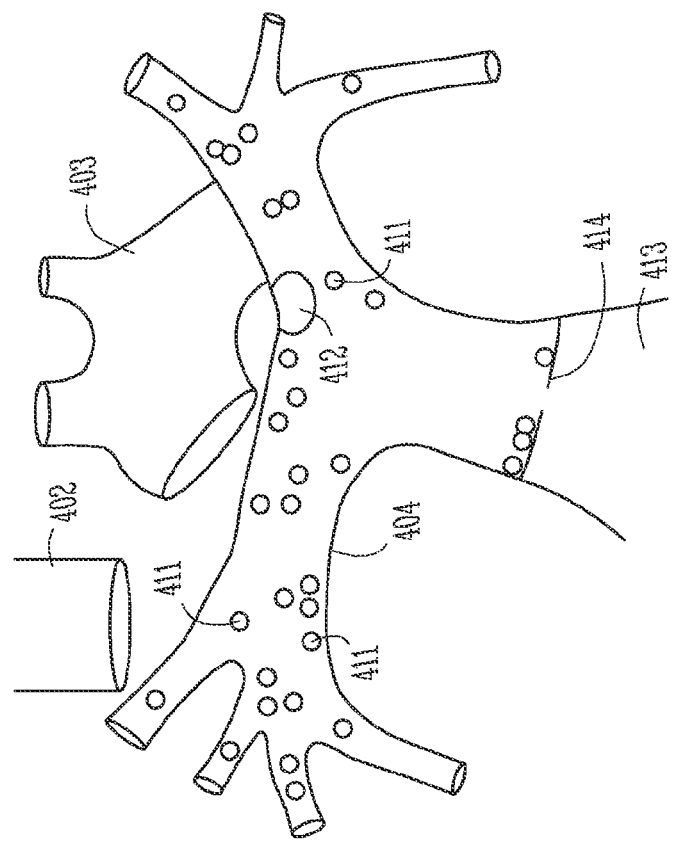
FIG. 4 illustrates baroreceptors in and around the pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412. FIG. 5 illustrates baroreceptor fields 512 in the aortic arch 503, near the ligamentum arteriosum and the trunk of the pulmonary artery 504. Some embodiments position the lead in the pulmonary artery to stimulate baroreceptor sites in the aorta and/or fat pads, such as are illustrated in FIGS. 2B-2C.

Figure 6:
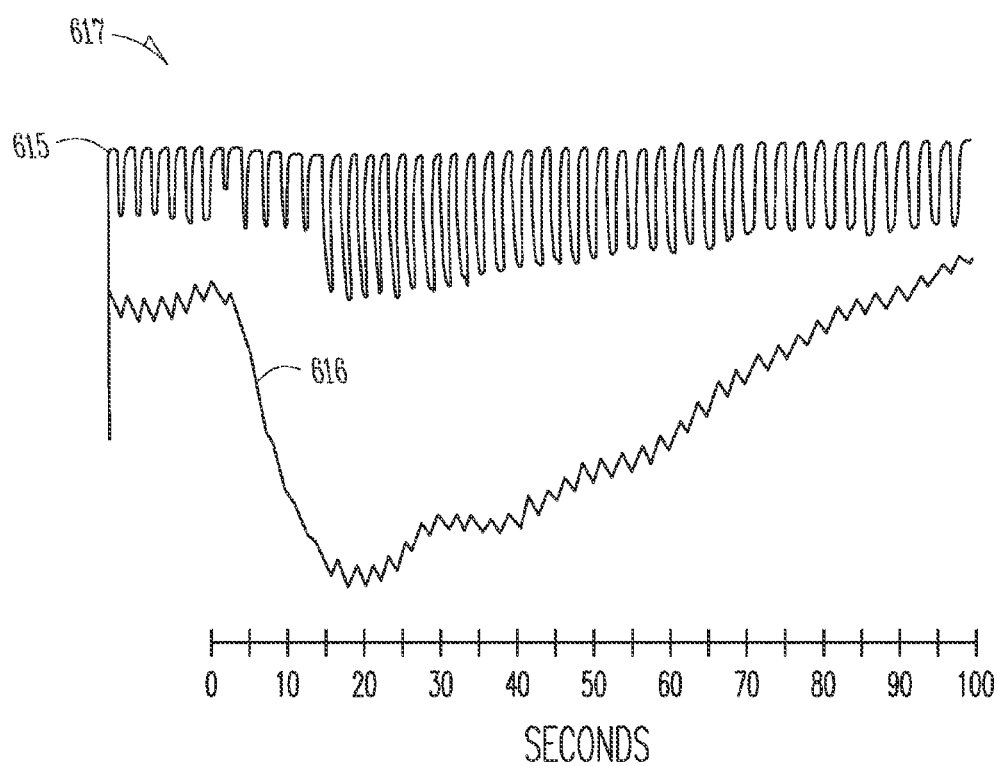
FIG. 6 illustrates a known relationship between respiration and blood pressure when the baroreflex is stimulated.

FIG. 6 illustrates a known relationship between respiration 615 and blood pressure 616 when the left aortic nerve is stimulated. When the nerve is stimulated at 617, the blood pressure 616 drops, and the respiration 615 becomes faster and deeper, as illustrated by the higher frequency and amplitude of the respiration waveform The respiration and blood pressure appear to return to the pre-stimulated state in approximately one to two minutes after the stimulation is removed. This relationship between respiration and blood pressure allows respiration to be used as a surrogate parameter for blood pressure.

Figure 7:
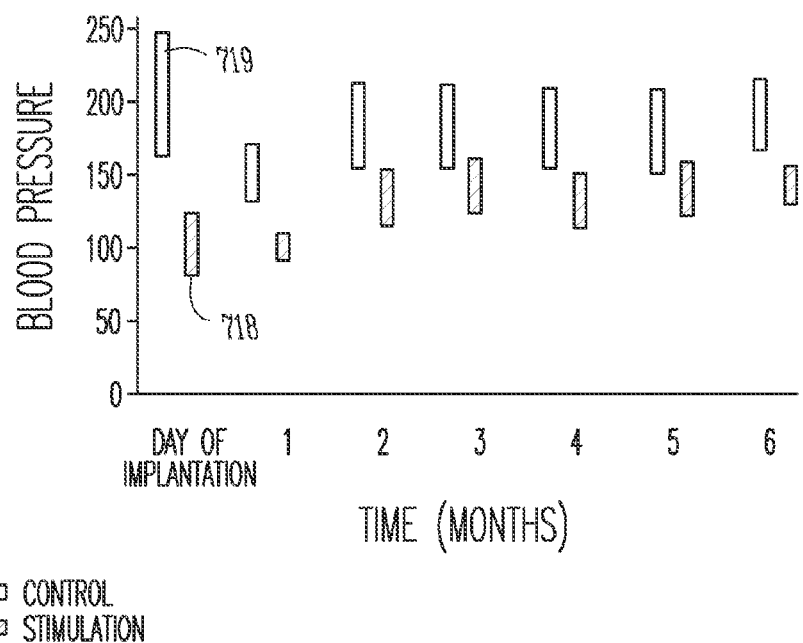
FIG. 7 illustrates a blood pressure response to carotid nerve stimulation in a hypertensive dog during 6 months of intermittent carotid nerve stimulation.

FIG. 7 illustrates a known blood pressure response to carotid nerve stimulation in a hypertensive dog during 6 months of intermittent carotid nerve stimulation. The carotid nerve stimulation involved turning on a carotid nerve stimulator once a month for up to six hours, and measuring the blood pressure response to monitor the stability of the acute response over long time periods. The figure illustrates that the blood pressure of a stimulated dog 718 is significantly less than the blood pressure of a control dog 719 that also has high blood pressure. Thus, such stimulation is capable of triggering the baroreflex to reduce high blood pressure.

Systems to Provide Neural Stimulation and CRM Therapies

Various embodiments of the present subject matter relate to neural stimulation and CRM therapies. Examples of neural stimulators include anti-hypertension (AHT) devices or AHT components that are used to treat hypertension. Various embodiments of the present subject matter include stand-alone implantable baroreceptor stimulator systems, include implantable devices that have integrated NS and cardiac rhythm management (CRM) components, and include systems with at least one implantable NS device and an implantable CRM device capable of communicating with each other either wirelessly or through a wire lead connecting the implantable devices. Although implantable systems are illustrated and discussed, various aspects and embodiments of the present subject matter can be implemented in external devices. Integrating NS and CRM functions, whether they are performed in the same or separate devices, improves aspects of the NS therapy and CRM therapy by allowing these therapies to intelligently work together.

Figure 8:
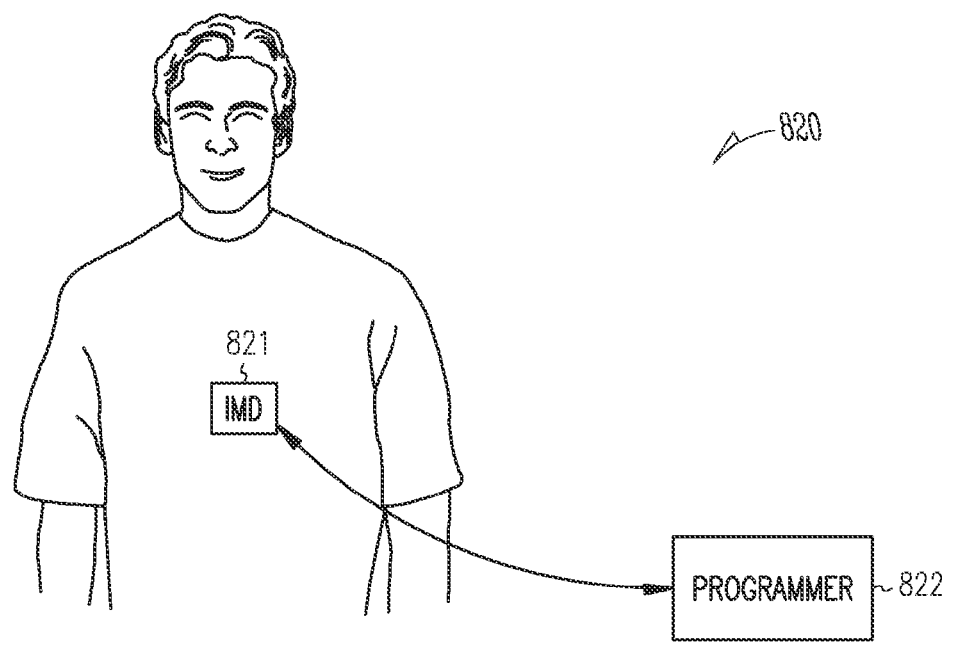
FIG. 8 illustrates a system including an implantable medical device (IMD) and a programmer, according to various embodiments of the present subject matter.

FIG. 8 illustrates a system 820 including an implantable medical device (IMD) 821 and a programmer 822, according to various embodiments of the present subject matter. Various embodiments of the IMD 821 include neural stimulator functions only, various embodiments include CRM functions only, and various embodiments include a combination of NS and CRM functions. Some embodiments of the neural stimulator provide AHT neural stimulation functions to treat hypertension. The programmer 822 and the IMD 821 are capable of wirelessly communicating data and instructions. In various embodiments, for example, the programmer 822 and IMD 821 use telemetry coils to wirelessly communicate data and instructions. Thus, the programmer can be used to adjust the programmed therapy provided by the IMD 821, and the IMD can report device data (such as battery and lead resistance) and therapy data (such as sense and stimulation data) to the programmer using radio telemetry, for example. According to various embodiments, the IMD 821 stimulates baroreceptors to provide NS therapy such as AHT therapy. Various embodiments of the IMD 821 stimulate baroreceptors in the pulmonary artery using a lead fed through the right ventricle similar to a cardiac pacemaker lead, and further fed into the pulmonary artery. Other embodiments stimulate other baroreceptor sites or baroreflex pathways. According to various embodiments, the IMD 821 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate baroreceptors and/or sense ANS activity.

Figure 9:
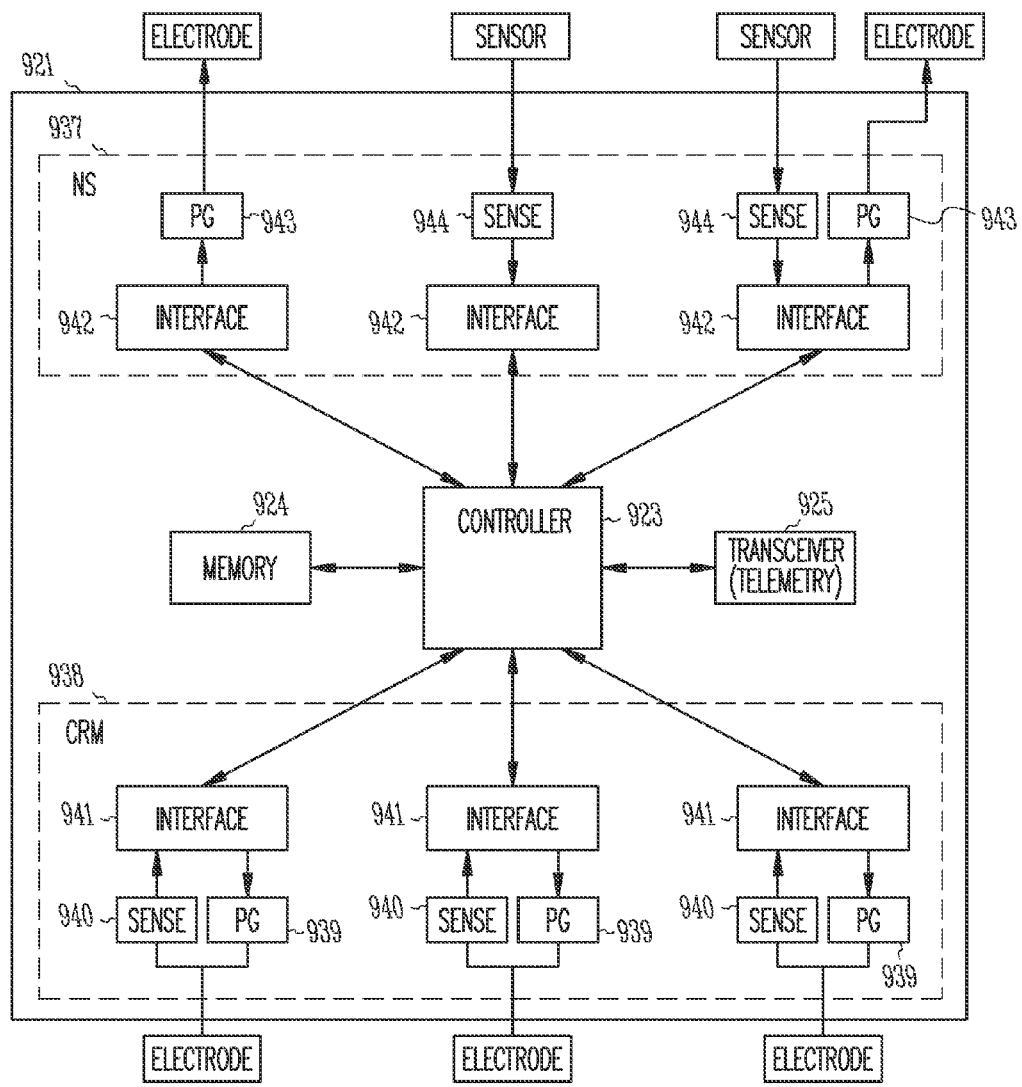
FIG. 9 illustrates an implantable medical device (IMD) such as shown in FIG. 8 having a neural stimulator (NS) component and cardiac rhythm management (CRM) component, according to various embodiments of the present subject matter.

FIG. 9 illustrates an implantable medical device (IMD) 921 such as shown at 821 in FIG. 8 having a neural stimulation (NS), such as an anti-hypertension (AHT) component 937 to treat hypertension, and cardiac rhythm management (CRM) component 938, according to various embodiments of the present subject matter. The illustrated device 921 includes a controller 923 and a memory 924. According to various embodiments, the controller 923 includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller 923 includes a processor to execute instructions embedded in memory to perform the baroreceptor stimulation and CRM functions. The illustrated device 921 further includes a transceiver 925 and associated circuitry for use to communicate with a programmer or another external or internal device. Various embodiments include a telemetry coil.

The CRM therapy section 938 includes components, under the control of the controller, to stimulate a heart and/or sense cardiac signals using one or more electrodes. The CRM therapy section includes a pulse generator 939 for use to provide an electrical signal through an electrode to stimulate a heart, and further includes sense circuitry 940 to detect and process sensed cardiac signals or otherwise detect pulsatile parameters according to the present subject matter. An interface 941 is generally illustrated for use to communicate between the controller 923 and the pulse generator 939 and sense circuitry 940. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 937 includes components, under the control of the controller, to stimulate a baroreceptor and/or sense ANS parameters associated with nerve activity or surrogates of ANS parameters such as blood pressure and respiration. Three interfaces 942 are illustrated for use to provide ANS therapy. However, the present subject matter is not limited to a particular number interfaces, or to any particular stimulating or sensing functions. Pulse generators 943 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 944 are used to detect and process signals from a sensor, such as a sensor of pulsatile parameters, and/or a sensor of nerve activity, blood pressure, respiration, and the like. The interfaces 942 are generally illustrated for use to communicate between the controller 923 and the pulse generator 943 and sense circuitry 944. Each interface, for example, may be used to control a separate lead. Various embodiments of the NS therapy section only include a pulse generator to stimulate baroreceptors. The NS therapy section is capable of providing AHT therapy to treat hypertension, for example.

An aspect of the present subject matter relates to a chronically-implanted stimulation system specially designed to treat hypertension by monitoring blood pressure and periodically stimulating baroreceptors or a baroreflex pathway using a stimulation protocol to activate the baroreflex and inhibit sympathetic discharge from the vasomotor center. Baroreceptors are located in various anatomical locations such as the carotid sinus and the aortic arch. Other baroreceptor locations include the pulmonary artery, including the ligamentum arteriosum, and sites in the atrial and ventricular chambers. Other baroreflex stimulation locations include baroreflex pathways such as ganglia in cardiac fat pads and afferent nerve trunks. In various embodiments, the system is integrated into a pacemaker/defibrillator or other electrical stimulator system. Components of the system include a pulse generator, sensors to monitor blood pressure or other pertinent physiological parameters, leads to apply electrical stimulation to baroreceptors, algorithms to determine the appropriate time to administer stimulation, and algorithms to manipulate data for display and patient management.

Various embodiments relate to a system that seeks to deliver electrically mediated NS therapy, such as AHT therapy, to patients. Various embodiments combine a "stand-alone" pulse generator with a minimally invasive, lead that stimulates baroreceptors and/or baroreflex pathways in the vicinity of the heart, such as in the pulmonary artery or cardiac fat pad(s), using direct or transvenous stimulation, for example. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, etc.) so as to maintain a desired quality of life. In various embodiments, an implanted system includes a pulse generating device and lead system, the stimulating electrode of which is positioned near endocardial baroreceptor tissues using transvenous implant technique(s). Another embodiment includes a system that combines NS therapy with traditional bradyarrhythmia, tachyarrhythmia, and/or congestive heart failure (CHF) therapies. Some embodiments use an additional "baroreceptor lead" that emerges from the device header and is paced from a modified traditional pulse generating system. In another embodiment, a traditional CRM lead is modified to incorporate proximal electrodes that are naturally positioned near baroreceptor sites. With these leads, distal electrodes provide CRM therapy and proximate electrodes stimulate baroreceptors.

A system according to these embodiments can be used to augment partially successful treatment strategies. As an example, undesired side effects may limit the use of some pharmaceutical agents. The combination of a system according to these embodiments with reduced drug doses may be particularly beneficial.

According to various embodiments, the lead(s) and the electrode(s) on the leads are physically arranged with respect to the heart in a fashion that enables the electrodes to properly transmit pulses and sense signals from the heart, and with respect to baroreceptors to stimulate the baroreflex. As there may be a number of leads and a number of electrodes per lead, the configuration can be programmed to use a particular electrode or electrodes. According to various embodiments, the baroreflex is stimulated by stimulating afferent nerve trunks.

Figure 10:
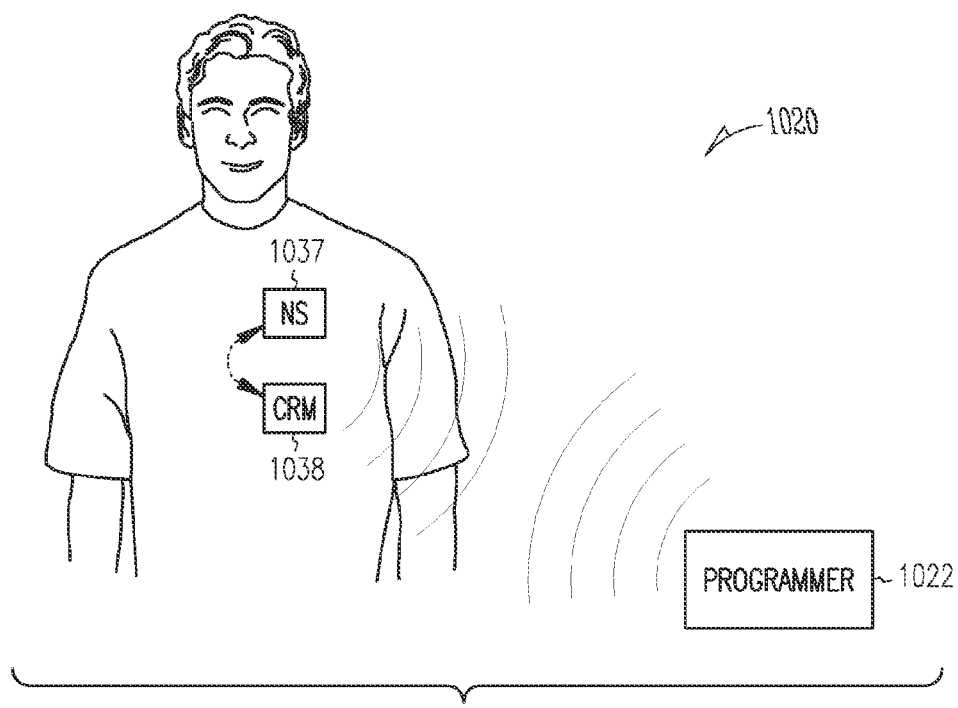
FIG. 10 illustrates a system including a programmer, an implantable neural stimulator (NS) device and an implantable cardiac rhythm management (CRM) device, according to various embodiments of the present subject matter.

FIG. 10 illustrates a system 1020 including a programmer 1022, an implantable neural stimulator (NS) device 1037 and an implantable cardiac rhythm management (CRM) device 1038, according to various embodiments of the present subject matter. Various aspects involve a method for communicating between an NS device 1037, such as an AHT device, and a CRM device 1038 or other cardiac stimulator. In various embodiments, this communication allows one of the devices 1037 or 1038 to deliver more appropriate therapy (i.e. more appropriate NS therapy or CRM therapy) based on data received from the other device. Some embodiments provide on-demand communications. In various embodiments, this communication allows each of the devices 1037 and 1038 to deliver more appropriate therapy (i.e. more appropriate NS therapy and CRM therapy) based on data received from the other device. The illustrated NS device 1037 and the CRM device 1038 are capable of wirelessly communicating with each other, and the programmer is capable of wirelessly communicating with at least one of the NS and the CRM devices 1037 and 1038. For example, various embodiments use telemetry coils to wirelessly communicate data and instructions to each other. In other embodiments, communication of data and/or energy is by ultrasonic means.

In some embodiments, the NS device 1037 stimulates the baroreflex to provide NS therapy. In some embodiments, the NS device 1037 further senses ANS activity directly or using surrogate parameters, such as respiration and blood pressure, indicative of ANS activity. The CRM device 1038 includes cardiac stimulation capabilities, such as pacing and defibrillating capabilities. In some embodiments, the CRM device provides pulsatile information. Rather than providing wireless communication between the NS and CRM devices 1037 and 1038, various embodiments provide a communication cable or wire, such as an intravenously-fed lead, for use to communicate between the NS device 1037 and the CRM device 1038.

Some NS device embodiments are able to be implanted in patients with existing CRM devices, such that the functionality of the NS device is enhanced by receiving physiological data that is acquired by the CRM device. The functionality of two or more implanted devices is enhanced by providing communication capabilities between or among the implanted devices. In various embodiments, the functionality is further enhanced by designing the devices to wirelessly communicate with each other.

According to various embodiments, for example, the NS device is equipped with a telemetry coil or ultrasonic transducer, allowing data to be exchanged between it and the CRM device. Embodiments of the NS device modify therapy based on electrophysiological parameters such as heart rate, minute ventilation, atrial activation, ventricular activation, and cardiac events. In addition, the CRM device modifies therapy based on data received from the NS device, such as mean arterial pressure, systolic and diastolic pressure, and baroreflex stimulation rate.

Figure 11:
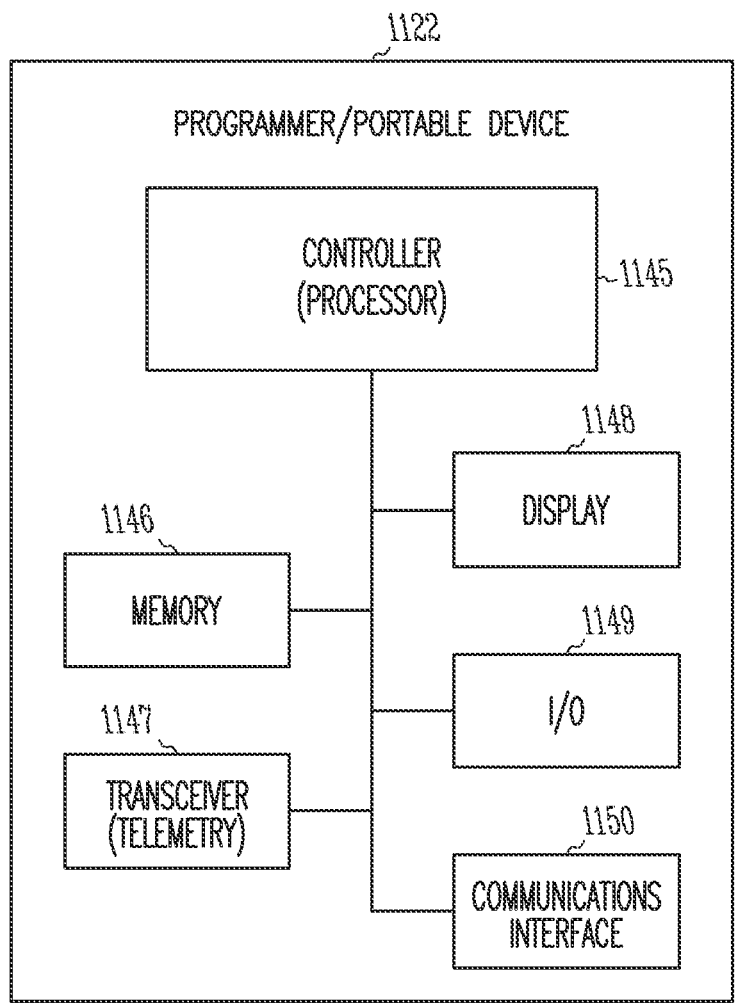
FIG. 11 illustrates a programmer such as illustrated in the systems of FIGS. 8 and 10 or other external device to communicate with the implantable medical device(s), according to various embodiments of the present subject matter.

FIG. 11 illustrates a programmer 1122, such as the programmer 822 and 1022 illustrated in the systems of FIGS. 8 and 10, or other external device to communicate with the implantable medical device(s) 1137 and/or 1138, according to various embodiments of the present subject matter. An example of another external device includes Personal Digital Assistants (PDAs) or personal laptop and desktop computers in an Advanced Patient Management (APM) system. The illustrated device 1122 includes controller circuitry 1145 and a memory 1146. The controller circuitry 1145 is capable of being implemented using hardware, software, and combinations of hardware and software. For example, according to various embodiments, the controller circuitry 1145 includes a processor to perform instructions embedded in the memory 1146 to perform a number of functions, including communicating data and/or programming instructions to the implantable devices. The illustrated device 1122 further includes a transceiver 1147 and associated circuitry for use to communicate with an implantable device. Various embodiments have wireless communication capabilities. For example, various embodiments of the transceiver 1147 and associated circuitry include a telemetry coil for use to wirelessly communicate with an implantable device. The illustrated device 1122 further includes a display 1148, input/output (I/O) devices 1149 such as a keyboard or mouse/pointer, and a communications interface 1150 for use to communicate with other devices, such as over a communication network.

The above-described functions of a system, whether implemented in two separate and distinct implantable devices or integrated as components into one or more implantable devices, includes, but is not limited to, processes for sensing electrical signals and filtering neural stimulation from the electrical signal. This disclosure refers to CRM devices that sense electrical signals such as electrograms. One of ordinary skill in the art will understand, upon reading and comprehending this disclosure, how to filter neural stimulation in other sensed electrical signals for use in other devices. The process can be performed by a processor executing computer-readable instructions embedded in memory, for example.

Figure 12:
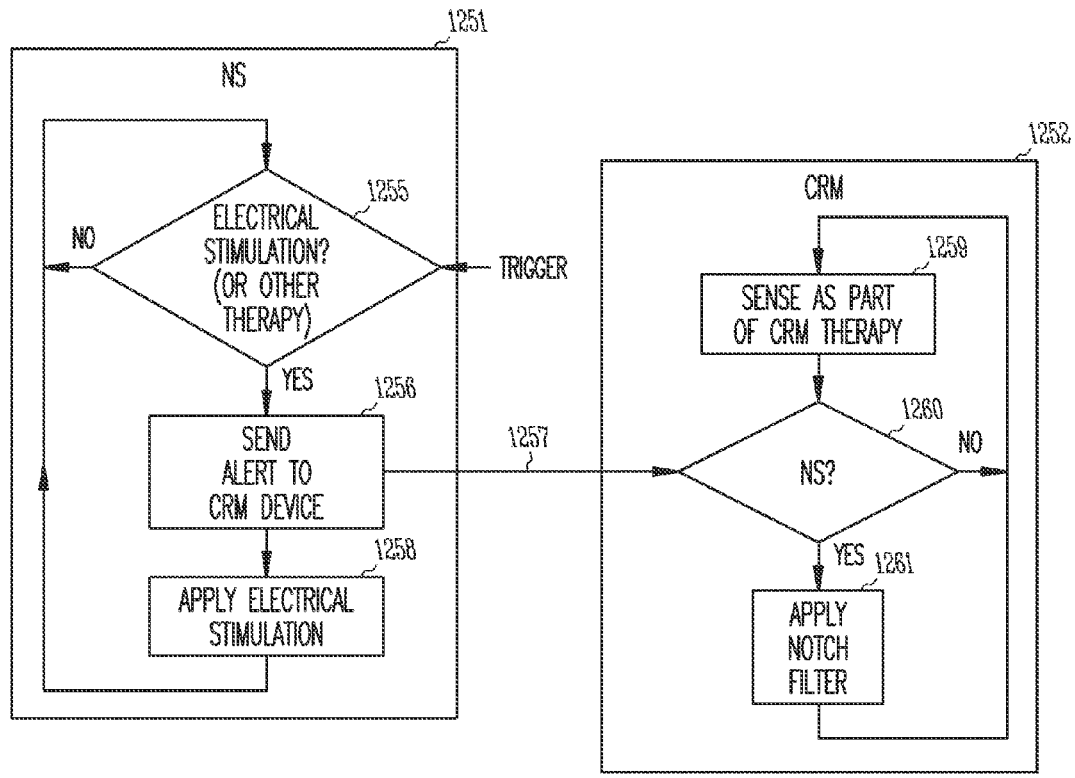
FIG. 12 illustrates interaction between neural stimulation (NS) and cardiac rhythm management (CRM) applications, according to various embodiments of the present subject matter.

FIG. 12 illustrates interaction between neural stimulation (NS) and cardiac rhythm management (CRM) applications, according to various embodiments of the present subject matter. Various embodiments provide the NS and CRM applications in a single device, and various embodiments provide the NS application in a first device and the CRM application in a second device.

The NS application 1251 includes determining whether electrical stimulation or other therapy is to be applied, as generally illustrated at 1255. If electrical stimulation is to be applied, an alert is sent via an alert signal 1257 to the CRM application 1252 at 1256, and the electrical stimulation is applied at 1258. The CRM application 1252 includes, as generally illustrated at 1259, sensing as part of a CRM therapy. This sensing can be referred to as a default sensing mode. This sensing includes sensing of electrical activity, such as electrograms to perform a desired CRM therapy. At 1260, the CRM application 1252 determines if a neural stimulation or other electrical stimulation is to be applied. Upon determining that neural stimulation is to be applied, a notch filter 1261 is applied. The application of the notch filter can also be referred to as a notch filter mode. The notch filter mode can be implemented via hardware, software or a combination of hardware and software.

Figure 13:
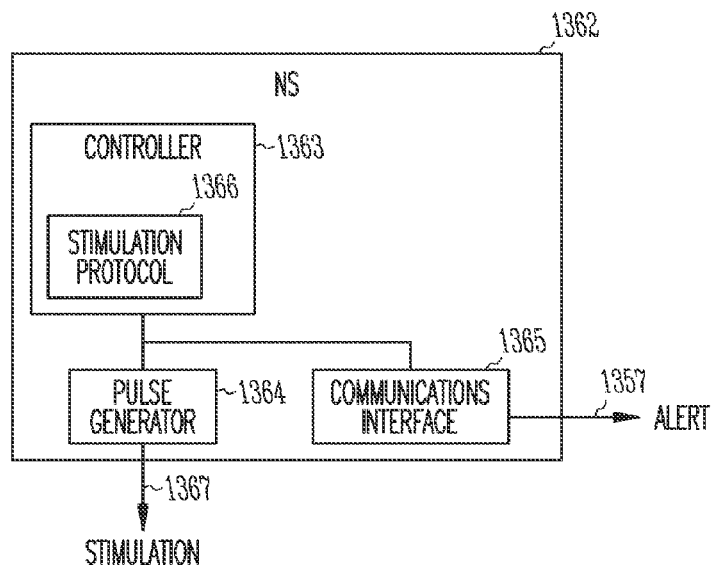
FIG. 13 illustrates a neural stimulation (NS) device, according to various embodiments of the present subject matter.

FIG. 13 illustrates a neural stimulation (NS) device 1362, according to various embodiments of the present subject matter. The illustrated NS device 1362 is capable of performing the NS application 1251 in FIG. 12. The illustrated NS device includes a controller 1363 adapted to communicate with a pulse generator 1364 and a communications interface 1365. The controller 1363 is adapted to implement a stimulation protocol 1366 to provide a desired neural stimulation 1367, such as a baroreflex stimulation therapy. Examples of baroreflex stimulation sites were previously discussed, and will not be repeated here. Although not expressly the illustrated, the neural stimulation can be applied using a lead and a variety of lead configurations. The controller and communications interface are adapted to provide a neural stimulation alert signal for use by another application 1357, such as a CRM application generally illustrated at 1252 in FIG. 12.

Figure 14A:
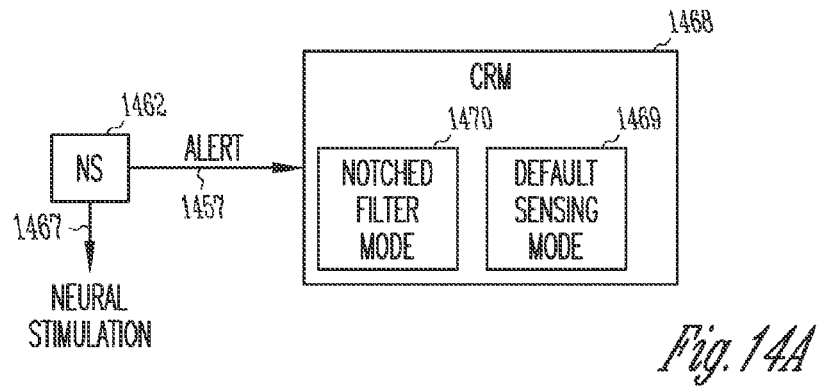
FIG. 14A illustrates an embodiment of a system that includes a neural stimulation (NS) device and a cardiac rhythm management (CRM) device adapted to switch from a default sensing mode to a notched filter mode when neural stimulation is applied by the NS device.
Figure 14B:
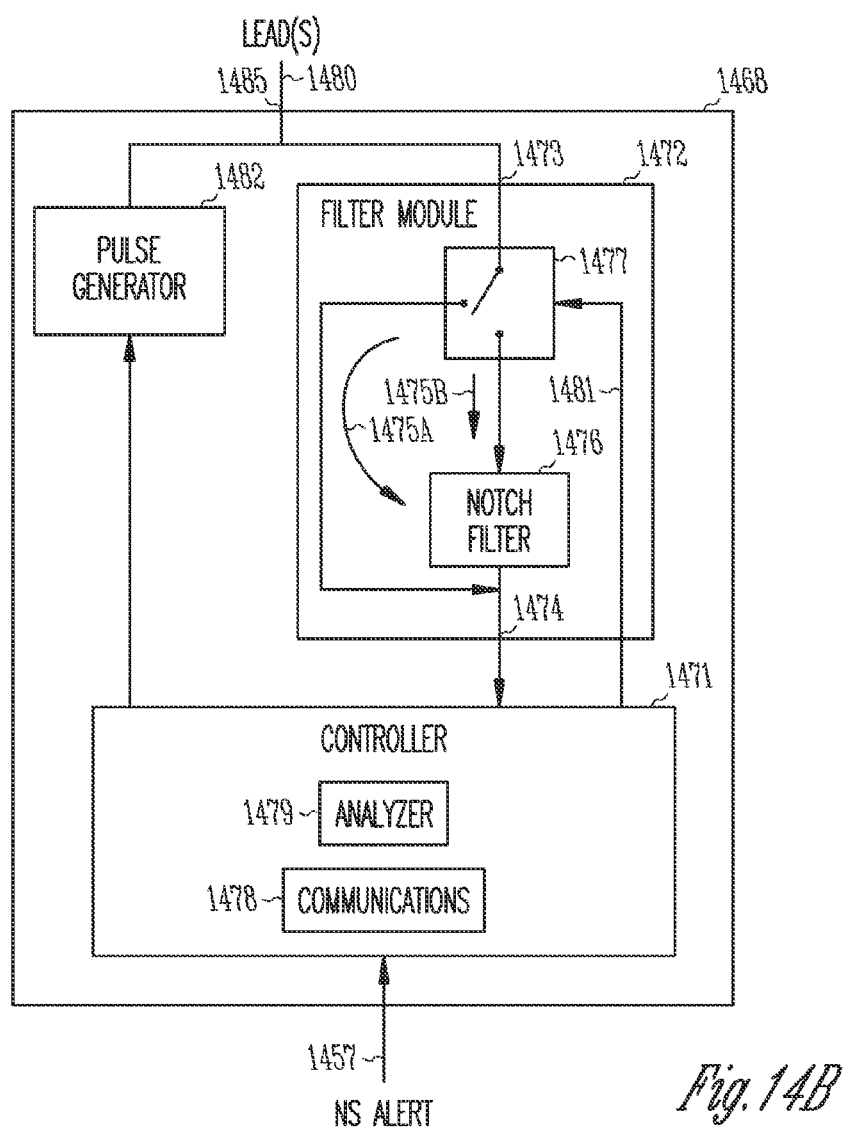
FIG. 14B illustrates an embodiment of a CRM device capable of being used in the system of FIG. 14A.

FIG. 14A illustrates an embodiment of a system that includes a neural stimulation (NS) device 1462 and a cardiac rhythm management (CRM) device 1468 adapted to switch from a default sensing mode 1469 to a notched filter mode 1470 when neural stimulation is applied by the NS device; and FIG. 14B illustrates an embodiment of a CRM device 1468 capable of being used in the system of FIG. 14A. In FIG. 14A, the NS device 1462 is adapted to apply neural stimulation 1467, and to transmit a neural stimulation alert signal 1457 to the CRM device 1468. The CRM device 1468 is adapted to implement a default sensing mode 1469, and to selectively implement a notched filter mode 1470 in response to receiving the neural stimulation alert signal 1457. The notched filter mode 1470 allows the CRM device to continue to effectively sense cardiac signal with the neural stimulation artifacts filtered from the signal.

The CRM device 1468 illustrated in FIG. 14B includes a controller 1471 and a filter module 1472. The filter module 1472 includes an input 1473, an output 1474, and a signal path (1475A or 1475B) from the input 1473 to the output 1474. The illustrated filter module 1472 has a notch filter 1476 and a switch 1477. The switch can include logical and physical switches. Various embodiments implement the switch as a transistor or solid state device. Various embodiments implement the switch in software. The notch filter 1476 has a center frequency corresponding to a frequency of a neural stimulation signal, such as signal 1467 in FIG. 14A. The switch is adapted to place the notch filter 1467 in the signal path (via path 1475B) when the neural stimulation signal is applied and to remove the notch filter from the signal path when the neural stimulation signal is not applied. The controller 1471 includes a communications module 1478 to receive a neural stimulation alert signal 1457, and an analyzer module 1479 to analyze cardiac signals received from one or more leads 1480 (attached via port 1485) and passed through the filter module 1472. The controller 1471 controls the switch 1477 in the filter module via control line 1481 to apply the notch filter when the controller receives a neural stimulation alert signal and remove the notch filter when the neural stimulation is not being applied. The illustrated CRM device 1468 includes a pulse generator 1482. The controller is adapted to implement a cardiac stimulation protocol to cause the pulse generator to provide a desired cardiac stimulation signal on one or more leads.

Figure 15A:
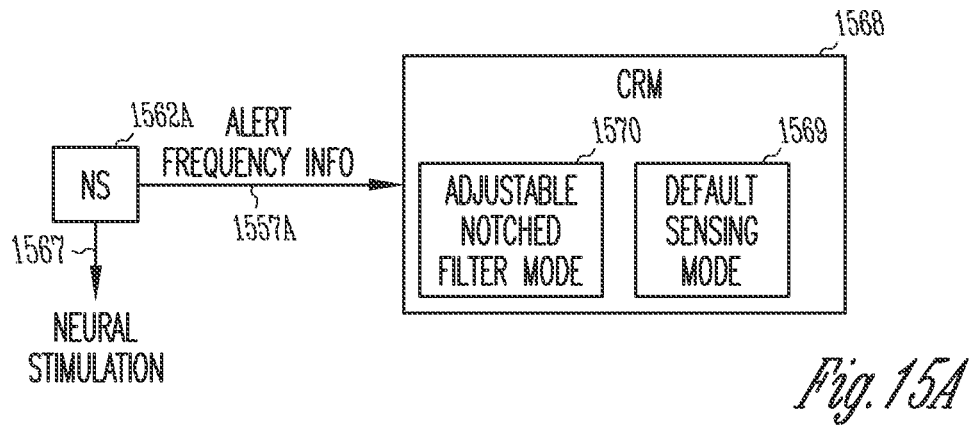
FIGS. 15A and 15B illustrate embodiments of a system that includes a neural stimulation (NS) device and a cardiac rhythm management (CRM) device adapted to switch from a default sensing mode to an adjustable notched filter mode based on an alert signal from the NS device.
Figure 15B:
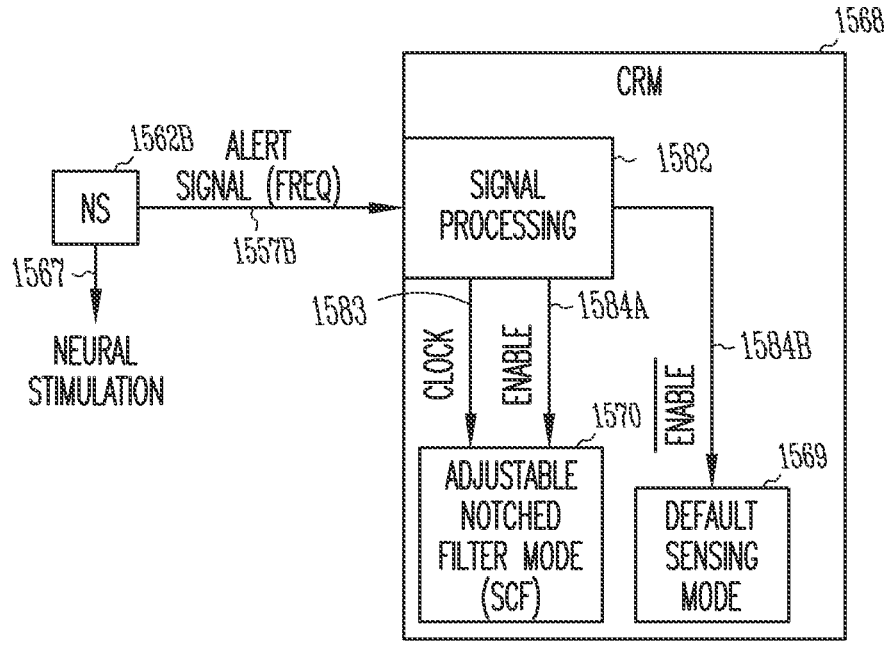
Figure 15C:
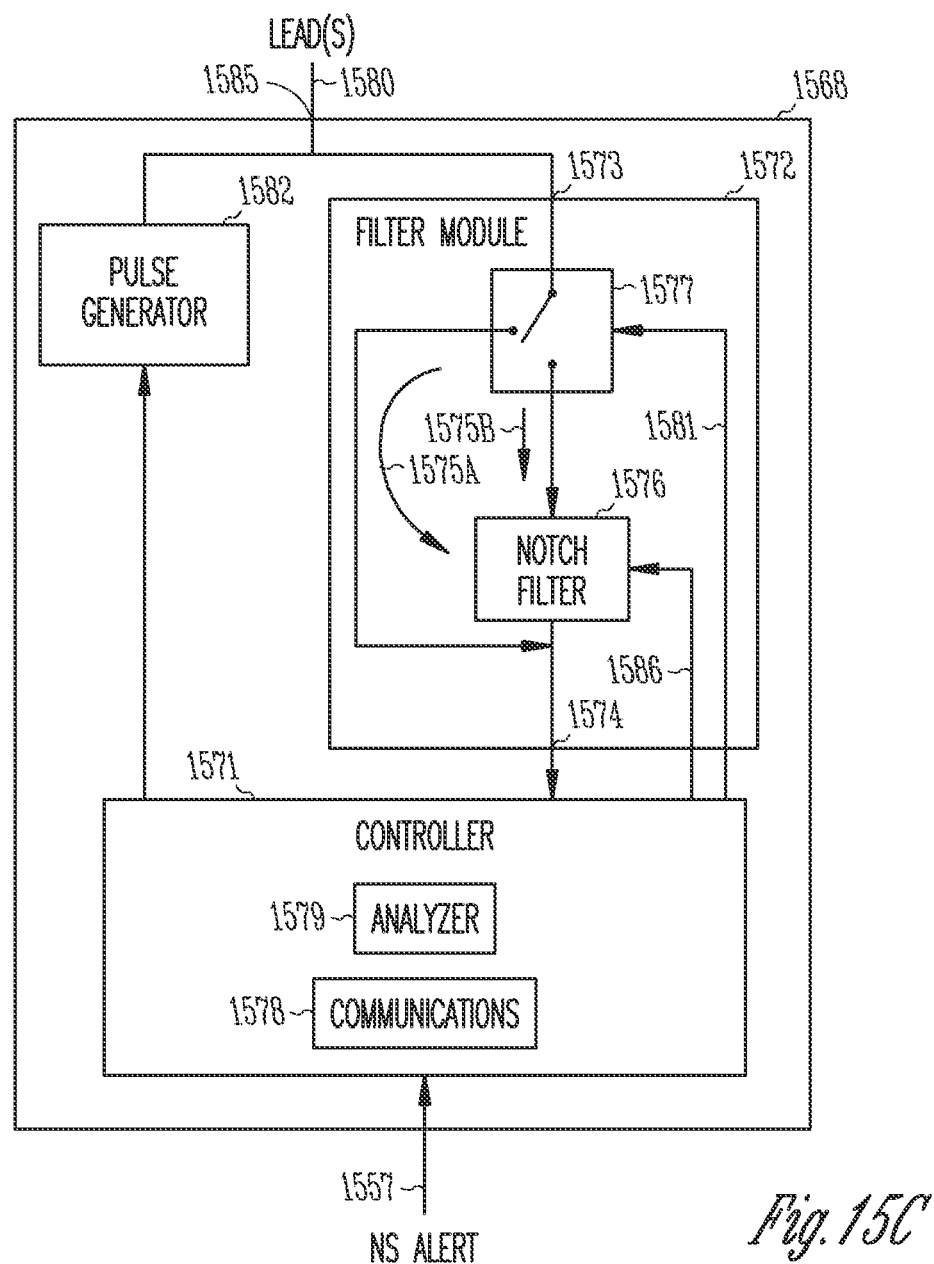
FIG. 15C illustrates an embodiment of a CRM device capable of being used in the systems of FIGS. 15A and 15B.

FIGS. 15A and 15B illustrate embodiments of a system that includes a neural stimulation (NS) device 1562 and a cardiac rhythm management (CRM) device 1568 adapted to switch from a default sensing mode 1569 to an adjustable notched filter mode 1570 based on an alert signal 1557A from the NS device 1562; and FIG. 15C illustrates an embodiment of a CRM device 1568 capable of being used in the systems of FIGS. 15A and 15B.

In FIG. 15A, the NS device 1562A is adapted to apply neural stimulation 1567, and to transmit a communication signal 1557A to the CRM device 1568. The communication signal 1557A includes a data signal that provides a neural stimulation alert and further provides information regarding the frequency of the neural stimulation. The CRM device 1568 is adapted to implement a default sensing mode 1569, and to selectively implement a notched filter mode 1570 in response to receiving the neural stimulation alert via the communication signal 1557A. The notched filter mode allows the CRM device to continue to sense cardiac signal with the neural stimulation artifacts filtered from the signal. The illustrated notch filter mode 1570 is identified as an adjustable notch filter because a center frequency of the notch filter can be changed based on the frequency of the neural stimulation as communicated using information in the data signal. The CRM device 1568 receives and processes the data signal 1557A to provide a control signal indicative of the neural stimulation frequency, which is used to select a desired center frequency of the notch filter to filter the neural stimulation from a sensed electrical signal.

In FIG. 15B, the NS device 1562B is adapted to apply neural stimulation 1567, and to transmit a communication signal 1557B to the CRM device 1568. The communication signal 1557B provides a neural stimulation alert. The illustrated NS device 1562B is adapted to transmit the communication signal 1557B with a frequency that corresponds to the frequency of the neural stimulation. The CRM device is adapted to implement a default sensing mode 1569, and to selectively implement a notched filter mode in response to receiving the neural stimulation alert signal via the communication signal 1557B. The illustrated notch filter mode is identified as an adjustable notch filter because a center frequency of the notch filter can be changed based on the frequency of the neural stimulation as communicated using information in the data signal. The CRM device includes a signal processing module 1582 to detect the frequency of the neural stimulation communication signal 1557B to provide a control signal 1583, illustrated as a clock signal, indicative of the neural stimulation frequency, which is used to select a desired center frequency of the notch filter 1570 to filter the neural stimulation from a sensed electrical signal. The signal processing module also provides an enable signal 1584A, based on a neural stimulation status signal, for use to trigger the notch filter mode and a complementary enable signal 1584B for use to trigger the default sensing mode.

The CRM device 1568 illustrated in FIG. 15C includes a controller 1571 and a filter module 1572. The filter module 1572 includes an input 1573, an output 1574, and a signal path (1575A or 1575B) from the input to the output. The illustrated filter module has a notch filter 1576 and a switch 1577. The switch 1577 is adapted to place the notch filter 1576 in the signal path (via path 1575B) when the neural stimulation signal is applied and to remove the notch filter from the signal path (via path 1575A) when the neural stimulation signal is not applied. The controller 1571 includes a communications module 1578 to receive a communication signal, and an analyzer module 1579 to analyze cardiac signals received from one or more leads 1580 (attached via port 1585) and passed through the filter module. The controller 1571 controls the switch 1577 in the filter module via control line 1581 to apply the notch filter when the controller receives a neural stimulation alert signal 1557 and remove the notch filter when the neural stimulation is not being applied. The notch filter has an adjustable center frequency adapted to correspond to a frequency of a neural stimulation signal. The controller 1571 adjusts the center frequency of the notch filter 1576 via control line 1586. The illustrated CRM device includes a pulse generator 1582. The controller 1571 is adapted to implement a cardiac stimulation protocol to cause the pulse generator to provide a desired cardiac stimulation signal on one or more leads 1580.

Figure 16A:
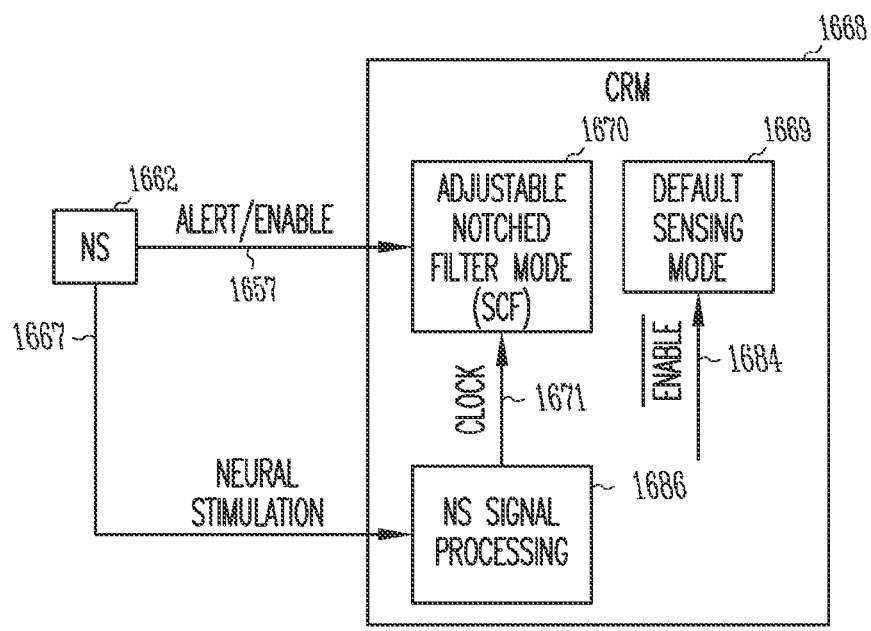
FIG. 16A illustrates an embodiment of a system that includes a neural stimulation (NS) device and a cardiac rhythm management (CRM) device adapted to switch from a default sensing mode to an adjustable notched filter mode based on an alert signal from the NS device and a sensed neural stimulation frequency.
Figure 16B:
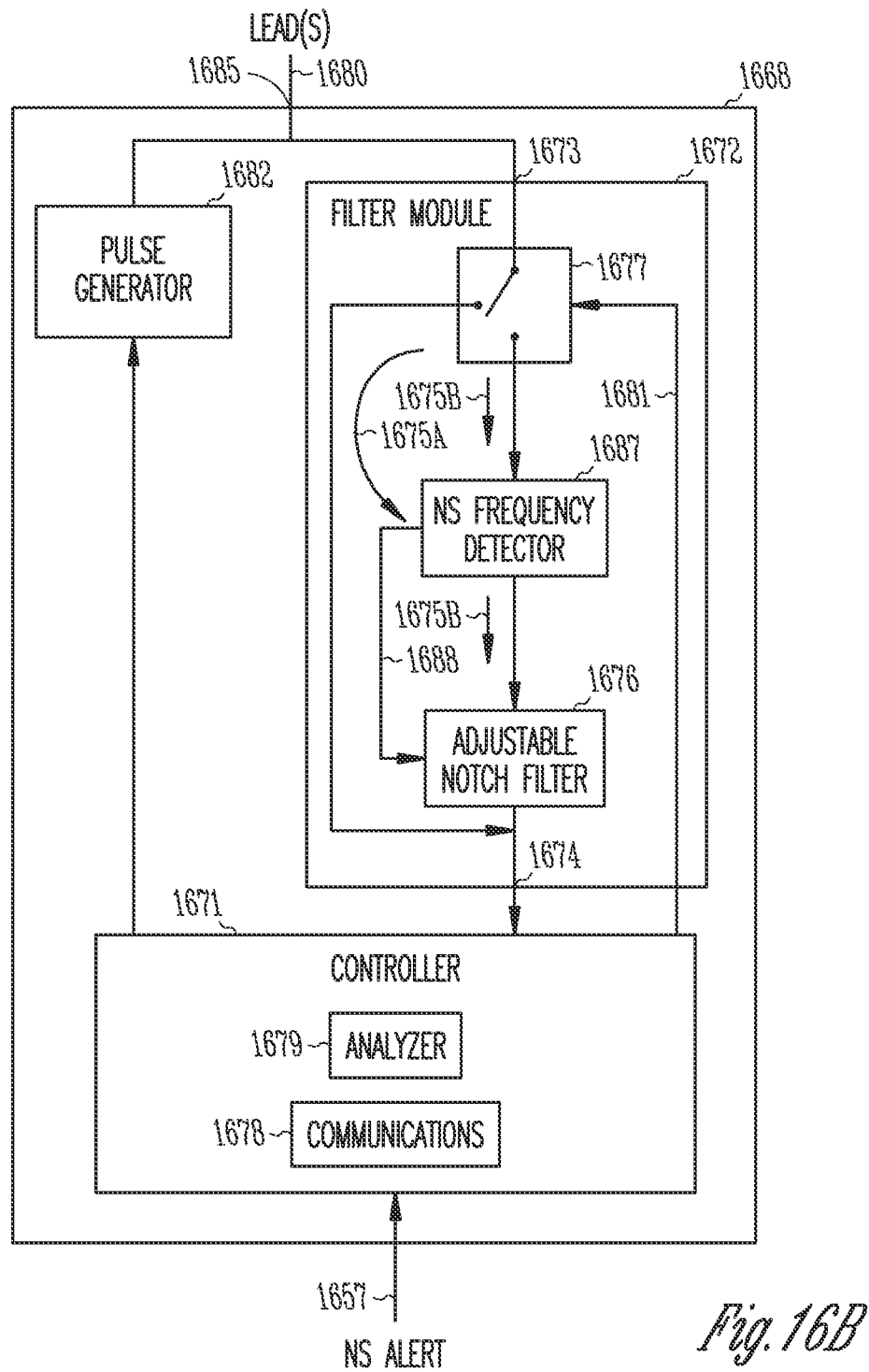
FIG. 16B illustrates an embodiment of a CRM device capable of being used in the systems of FIG. 16A.

FIG. 16A illustrates an embodiment of a system that includes a neural stimulation (NS) device 1662 and a cardiac rhythm management (CRM) device 1668 adapted to switch from a default sensing mode 1669 to an adjustable notched filter mode 1670 based on an alert signal from the NS device and a sensed neural stimulation frequency; and FIG. 16B illustrates an embodiment of a CRM device capable of being used in the systems of FIG. 16A.

In FIG. 16A, the NS device 1662 is adapted to apply neural stimulation 1667, and to transmit a communication signal 1657 to the CRM device 1668. The communication signal provides a neural stimulation alert 1657. The CRM device is adapted to implement a default sensing mode 1669, and to selectively implement a notched filter mode 1670 in response to receiving the neural stimulation alert signal 1657. The notched filter mode allows the CRM device to continue to sense cardiac signal with the neural stimulation artifacts filtered from the signal. The illustrated notch filter mode 1670 is identified as an adjustable notch filter because a center frequency of the notch filter can be changed based on the frequency of the neural stimulation. The CRM device 1668 includes a neural stimulation (NS) signal processing module 1686 to detect the frequency of the neural stimulation to provide a control signal, illustrated as a clock signal 1671, indicative of the neural stimulation frequency, which is used to select a desired center frequency of the notch filter to filter the neural stimulation from a sensed electrical signal. An enable signal (illustrated as alert signal 1657) for use to trigger the notch filter mode 1670 and a complementary enable signal 1684 for use to trigger the default sensing mode are based upon the neural stimulation alert signal.

The CRM device 1668 illustrated in FIG. 16B includes a controller 1671 and a filter module 1672. The filter module 1672 includes an input 1673, an output 1674, and a signal path (1675A or 1675B) from the input to the output. The illustrated filter module has a notch filter 1676 and a switch 1677. The switch is adapted to place the notch filter 1676 in the signal path (via path 1675B) when the neural stimulation signal is applied and to remove the notch filter from the signal path (via path 1675A) when the neural stimulation signal is not applied. The controller 1671 includes a communications module 1678 to receive a neural stimulation alert signal, and an analyzer module 1679 to analyze cardiac signals received from one or more leads (attached via port 1685) and passed through the filter module. The controller controls the switch in the filter module via control line 1681 to apply the notch filter when the controller receives a neural stimulation alert signal and remove the notch filter when the neural stimulation is not being applied. The notch filter 1676 has an adjustable center frequency adapted to correspond to a frequency of a neural stimulation signal. The filter module 1672 includes a neural stimulation (NS) frequency detector 1676 which provides a control signal via control line 1688 to the adjustable notch filter 1676 for use to adjust the center frequency of the notch filter. The illustrated CRM device includes a pulse generator 1682. The controller 1671 is adapted to implement a cardiac stimulation protocol to cause the pulse generator 1682 to provide a desired cardiac stimulation signal on one or more leads 1680.

Various embodiments of the adjustable notch filter, such as illustrated a 1576 in FIG. 15C and at 1676 in FIG. 16B, include a switched-capacitor filter (SCF). SCFs are capable of being configured as a notch filter to remove an unwanted frequency (or a small frequency range) from a signal, while affecting all other frequencies as little as possible. The present subject matter uses a notch filter to remove a neural stimulation frequency (or a frequency range containing the neural stimulation frequency) while affecting the other frequencies corresponding to the electrogram signal as little as possible. Thus, the analyzer can still detect useful information from the electrogram at times of neural stimulation.

SCFs are accurate and easy-to-use filters that do not require external capacitors and/or inductors. Integrated-circuit SCFs have tightly matched and trimmed internal capacitors that produce a fixed frequency and phase response that are proportional solely to the external clock frequency. The cutoff frequencies of the filter are proportional to and determined only by the external clock frequency. Various embodiments of the present subject matter use a neural stimulation signal, or a control signal derived from the neural stimulation signal, as the external clock frequency to set the center frequency of the notch file. SCFs are clocked, sampled-data systems. The input signal is sampled at a high rate and is processed on a discrete-time, rather than continuous basis.

The above disclosure, and accompanying figures, refer to a notched filter. As developed below, various embodiments of the present subject matter use multiple notched filters, and various embodiments of the present subject mater use a low pass filter. Those of ordinary skill in the art will understand, upon reading and comprehending this disclosure, how to implement the present subject matter with multiple notched filters and low pass filters.

Figure 17A:
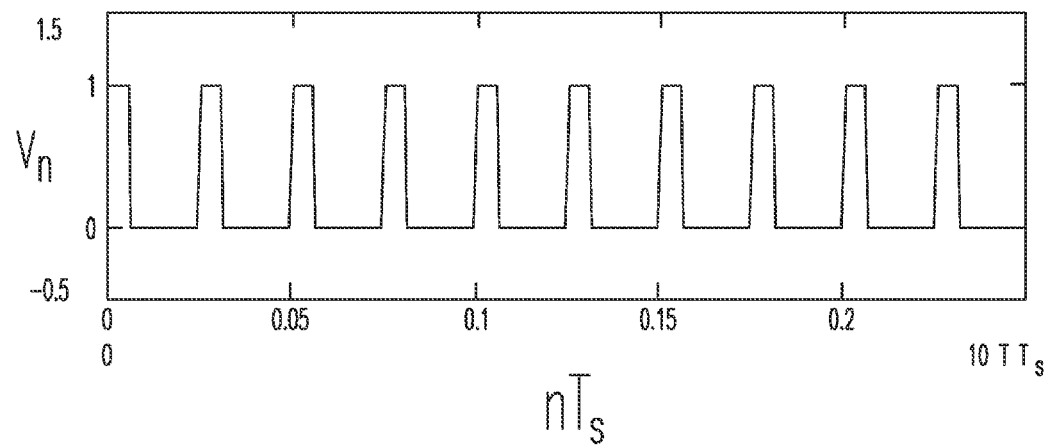
FIGS. 17A, 17B, and 17C illustrate a 40 Hz rectangular wave with a 5 ms pulse width, corresponding harmonic energy, and filter transfer responses for two notched filters to filter the first and second harmonic frequencies, respectively, to illustrate an example of multiple notch filters according to various embodiments of the present subject matter.
Figure 17B:
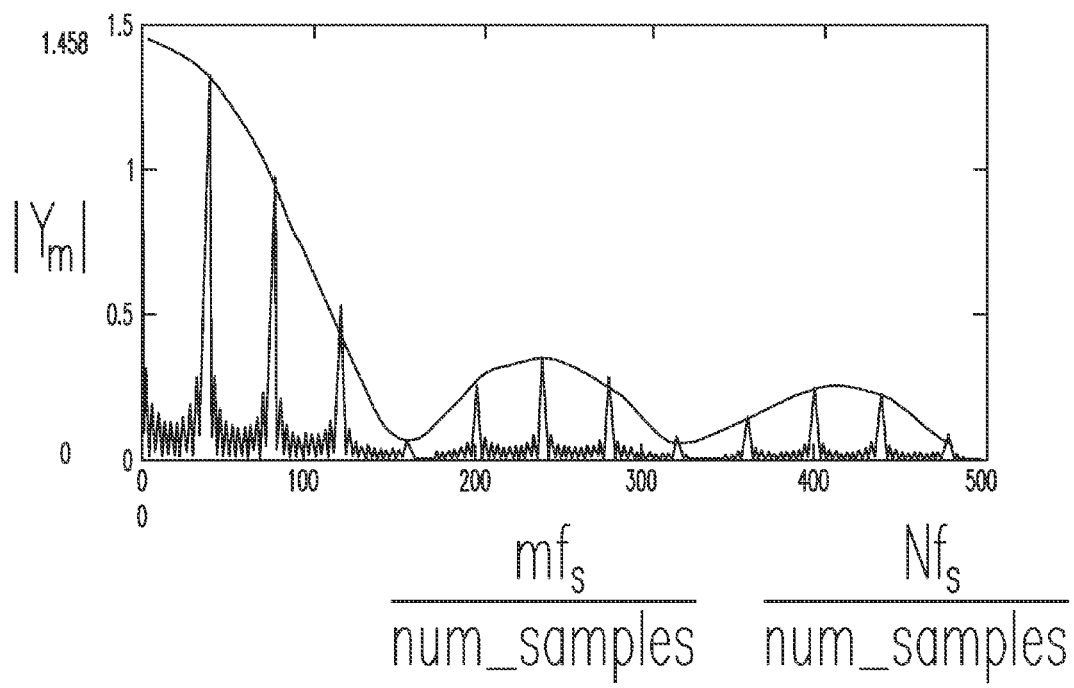
Figure 17C:
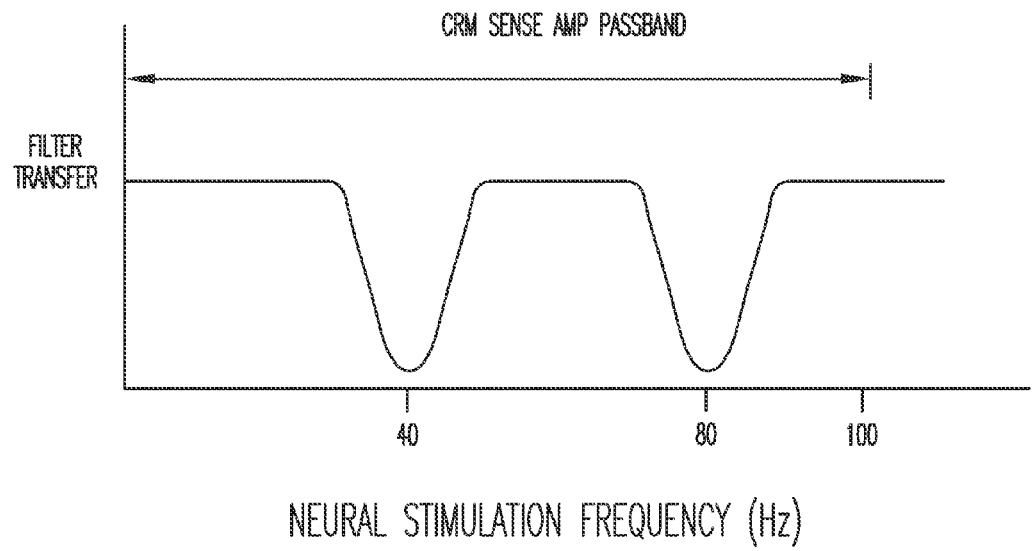

A sense amplifier, such as sense amplifier fir a CRM device, has a passband. Frequencies that fall within the passband are capable of being sensed by the sense amplifier. The neural stimulation signal, along with one or more harmonics, may fall within the sense amplifier passband. For example, a 40 Hz neural stimulation signal has energy at 80 Hz, 120 Hz, etc., where in this example 40 Hz is referred to as the first harmonic, 80 Hz. is referred to as the second harmonic, 120 Hz is referred to as the third harmonic, and so forth. FIGS. 17A, 17B, and 17C illustrate a 40 Hz rectangular wave with a 5 ms pulse width, corresponding harmonic energy, and filter transfer responses for two notched filters to filter the first and second harmonic frequencies, respectively, to illustrate an example of multiple notch filters according to various embodiments of the present subject matter. The wave shape and frequency are provided by way of example, and not by way of limitation. The spectra of a rectangular wave has energy at DC and at the harmonics of the repetition rate. A blocking capacitor can be used to block the DC energy. As illustrated in FIG. 17B, the amplitude of the harmonics is bounded by a sine function, which is also referred to as an interpolation or filtering function. The sine function is the product of a sine function and a monotonically decreasing function.

If the sense amplifier passband extends to 100 Hz, the neural stimulation energy at 40 Hz and 80 Hz may be sensed by the sense amplifier. In this example, as illustrated in FIG. 17C, a first notched filter with a center frequency of approximately 40 Hz and a second notched filter with a center frequency of approximately 80 Hz can be used to filter the neural stimulation energy associated with the first and second harmonics of the neural stimulation signal. If multiple harmonics fall within the passband of the sense amplifier, multiple notched filters are used to filter out the harmonics. The center frequencies of the notched filters correspond to the harmonic frequencies that fall with in the sense amplifier pass band.

Figure 18:
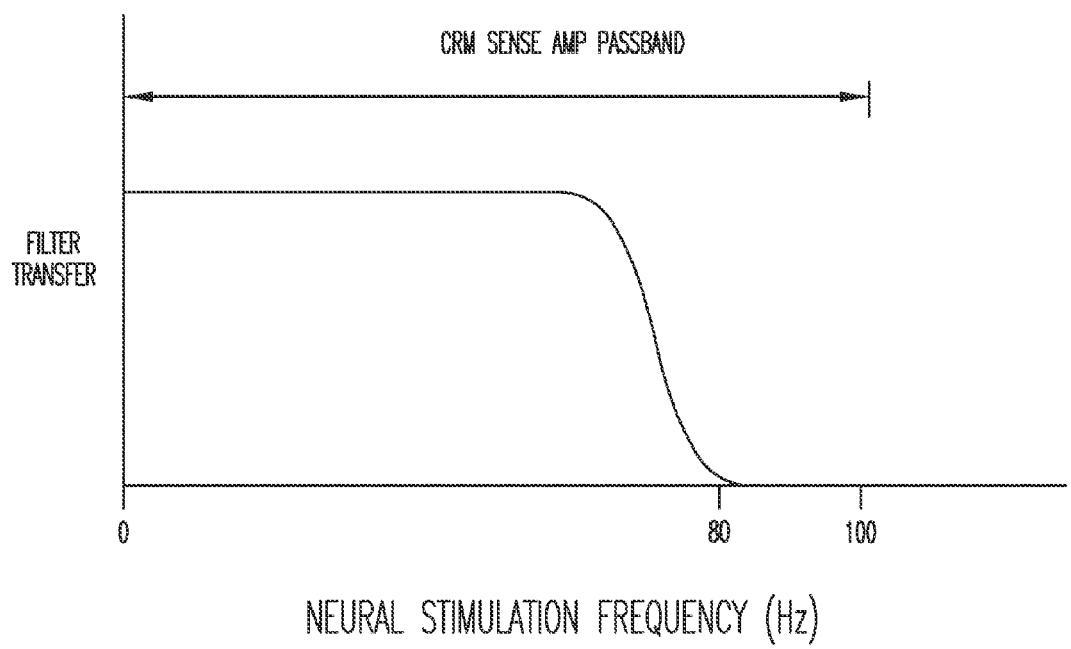
FIG. 18 illustrates a filter transfer response for a lowpass filter to attenuate the first harmonic of the neural stimulation signal and higher frequencies, according to various embodiments of the present subject matter.

Various embodiments of the present subject matter use a lowpass filter if the neural stimulation frequency is toward the upper range of the sense amplifier passband (e.g. 80 Hz neural stimulation and a sense amplifier passband extending to 100 Hz). FIG. 18 illustrates a filter transfer response for a lowpass filter to attenuate the first harmonic of the neural stimulation signal and higher frequencies, according to various embodiments of the present subject matter. According to various embodiments, the lowpass filter is implemented using existing sense amplifier hardware with less phase distortion than a notch filter.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired neural stimulation (NS) or anti-hypertension (AHT) therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A medical device, comprising:
   a filter module to pass electrical signals indicative of sensed electrical activity over a signal path, the filter module including a filter selectively connected in the signal path, the filter having a transfer response to attenuate a frequency of a neural stimulation signal; and
   a controller to receive a neural stimulation status signal indicative of whether the neural stimulation signal is present, the neural stimulation status signal being a different signal than the electrical signals indicative of sensed electrical activity, the controller to communicate with the filter module and respond to the neural stimulation status signal to route the signal path through the filter when the neural stimulation signal is present to filter the neural stimulation frequency from the electrical signals and to remove the filter from the signal path when the neural stimulation signal is not present.

2. The device of claim 1, further comprising a sense amplifier with a sense amplifier passband, wherein the frequency of the neural stimulation signal is near an upper range of the sense amplifier passband, and the filter includes a low pass filter to attenuate frequencies approximately equal to and higher than the frequency of the neural stimulation signal.

3. The device of claim 1, wherein the filter includes a notch filter having a center frequency corresponding to the frequency of the neural stimulation signal.

4. The device of claim 3, wherein the filter further includes a second notch filter having a center frequency corresponding to a second harmonic frequency for the frequency of the neural stimulation signal.

5. The device of claim 3, wherein the filter includes a plurality of notch filters, each having a center frequency corresponding to a unique one of a plurality of harmonic frequencies for the frequency of the neural stimulation signal.

6. The device of claim 3, wherein the notch filter includes an adjustable notch filter with an adjustable center frequency.

7. The device of claim 6, wherein the adjustable notch filter includes a switched capacitor filter, the switched capacitor filter to receive a clock signal having a clock frequency corresponding to the frequency of the neural stimulation signal to provide a desired center frequency.

8. The device of claim 7, further including a neural stimulation frequency detector to extract the clock signal from the neural stimulation signal.

9. The device of claim 7, further comprising:
communication circuitry to receive a communication signal regarding the neural stimulation, the communication signal having a frequency corresponding to the neural stimulation signal; and
a communication signal frequency detector to extract the clock signal from the frequency of the communication signal.

10. The device of claim 6, further comprising:
communication circuitry to receive a communication signal regarding the neural stimulation, the communication signal including frequency data indicative of the frequency of the neural stimulation signal; and
signal processing circuitry to provide a control signal corresponding to the frequency data to the adjustable notch filter to provide a desired center frequency.

11. The device of claim 1, further comprising a lead electrically connected to the signal path in the filter module, the lead including at least one electrode for use in sensing electrical activity.

12. The device of claim 1, further comprising a pulse generator to generate stimulation pulses, the controller to control the pulse generator to provide stimulator pulses for use in a desired stimulation therapy.

13. The device of claim 1, wherein the controller includes an analyzer to analyze the electrical signals indicative of sensed electrical activity.

14. The device of claim 1, wherein the device is an implantable cardiac rhythm management (CRM) device, the device further comprising a pulse generator to generate stimulation pulses for transmission through a lead, wherein the controller is adapted to control the pulse generator to provide stimulator pulses for use in a desired cardiac stimulation therapy, and wherein the controller is adapted to implement a sensing protocol to analyze the electrical signals indicative of sensed electrical activity.

15. The device of claim 14, wherein the controller of the CRM device is adapted to implement a default CRM sensing protocol, and upon receiving a neural stimulation alert from the neural stimulation status signal, to implement a notched filter protocol to connect the notch filter in the signal path to filter the neural stimulation frequency.

16. A medical device for filtering a sensed signal to attenuate a sensed neural stimulation signal that has a therapeutically-effective frequency, comprising:
a signal path for passing electrical signals indicative of a sensed electrical activity;
a filter with a transfer response to attenuate the therapeutically-effective frequency of the neural stimulation signal;
a switch configured to place the filter in the signal path and remove the filter from the signal path; and
a controller to receive a neural stimulation status signal indicative of whether the neural stimulation signal is being applied, the neural stimulation status signal being a different signal than the electrical signals indicative of electrical activity, the controller to control the switch to place the filter in the signal path when the neural stimulation signal is applied and to remove the filter from the signal path when the neural stimulation signal is not applied.

17. The device of claim 16, further comprising a sense amplifier with a sense amplifier passband, wherein the frequency of the neural stimulation signal is near an upper range of the sense amplifier passband, and the filter includes a low pass filter to attenuate frequencies approximately equal to and higher than the frequency of the neural stimulation signal.

18. The device of claim 16, wherein the filter includes a notch filter having a center frequency corresponding to the frequency of the neural stimulation signal.

19. The device of claim 18, wherein the notch filter includes an adjustable notch filter with an adjustable center frequency.

20. The device of claim 19, wherein the device is configured to automatically adjust the center frequency of the adjustable notch filter based on the therapeutically-effective frequency of the sensed neural stimulation signal.

* * * * *